(12) United States Patent
Hinsby et al.

(10) Patent No.: US 11,253,505 B2
(45) Date of Patent: Feb. 22, 2022

(54) ARIMOCLOMOL FOR TREATING GLUCOCEREBROSIDASE ASSOCIATED DISORDERS

(71) Applicant: Orphazyme A/S, Copenhagen N (DK)

(72) Inventors: Anders Mørkeberg Hinsby, Hellerup (DK); Thomas Kirkegaard Jensen, Rødovre (DK); Catherine Kolster Fog-Tonnesen, Brønshøj (DK); Nikolaj Havnsøe Torp Petersen, Copenhagen Ø (DK); Claus Bornæs, Hellerup (DK)

(73) Assignee: Orphazyme A/S, Copenhagen N (DK)

(*) Notice: Subject to any disclaimer, the term of this patent is extended or adjusted under 35 U.S.C. 154(b) by 20 days.

(21) Appl. No.: 16/879,198

(22) Filed: May 20, 2020

(65) Prior Publication Data

US 2020/0289497 A1 Sep. 17, 2020

Related U.S. Application Data

(63) Continuation of application No. 16/092,070, filed as application No. PCT/EP2017/060205 on Apr. 28, 2017.

(30) Foreign Application Priority Data

Apr. 29, 2016 (DK) .............................. PA201670281

(51) Int. Cl.
*A61K 31/4545* (2006.01)
*A61K 45/06* (2006.01)
*A61P 3/00* (2006.01)

(52) U.S. Cl.
CPC .......... *A61K 31/4545* (2013.01); *A61K 45/06* (2013.01); *A61P 3/00* (2018.01)

(58) Field of Classification Search
CPC .................................................. A61K 31/4545
See application file for complete search history.

(56) References Cited

U.S. PATENT DOCUMENTS

| | | | |
|---|---|---|---|
| 5,348,945 A | 9/1994 | Berberian et al. |
| 5,830,464 A | 11/1998 | Srivastava |
| 5,948,646 A | 9/1999 | Srivastava |
| 5,985,270 A | 11/1999 | Srivastava |
| 6,007,821 A | 12/1999 | Srivastava et al. |
| 6,139,841 A | 10/2000 | Srivastava |

(Continued)

FOREIGN PATENT DOCUMENTS

| | | |
|---|---|---|
| EP | 0751957 | 9/1995 |
| EP | 2145896 | 1/2010 |

(Continued)

OTHER PUBLICATIONS

Schapira, Molecular and Cellular Neuroscience, 2015;66:37-42 (Year: 2015).*

(Continued)

*Primary Examiner* — San Ming R Hui
(74) *Attorney, Agent, or Firm* — Cooley LLP; Ivor R. Elrifi; Heidi A. Erlacher

(57) ABSTRACT

The present invention relates to an active pharmaceutical ingredient selected from N-[2-hydroxy-3-(1-piperidinyl)-propoxy]-pyridine-1-oxide-3-carboximidoyl chloride, its stereoisomers and the acid addition salts thereof (arimoclomol), for use in a method of treating glucocerebrosidase associated disorders.

9 Claims, 12 Drawing Sheets

(56) References Cited

U.S. PATENT DOCUMENTS

| | | |
|---|---|---|
| 6,187,312 B1 | 2/2001 | Srivastava |
| 6,375,953 B1 | 4/2002 | Srivastava et al. |
| 6,384,029 B1 | 5/2002 | Jednakovits et al. |
| 6,403,095 B1 | 6/2002 | Srivastava et al. |
| 6,475,490 B1 | 11/2002 | Srivastava et al. |
| 6,649,628 B1 | 11/2003 | Kurthy et al. |
| 6,653,326 B1 | 11/2003 | Vigh et al. |
| 6,855,802 B1 | 2/2005 | Triebel et al. |
| 7,070,785 B2 | 7/2006 | Lehner et al. |
| 7,125,843 B2 | 10/2006 | DeFrees et al. |
| 7,126,002 B2 | 10/2006 | Urogdi et al. |
| 7,148,239 B2 | 12/2006 | Vigh et al. |
| 7,326,574 B2 | 2/2008 | Boux et al. |
| 7,361,655 B2 | 4/2008 | Csakai et al. |
| 7,384,936 B2 | 6/2008 | Csakai et al. |
| 7,396,681 B1 | 7/2008 | Multhoff |
| 7,517,948 B2 | 4/2009 | Multhoff |
| 7,550,457 B2 | 6/2009 | Csakai et al. |
| 7,691,849 B2 | 4/2010 | Csakai et al. |
| 7,745,465 B2 | 6/2010 | Vigh et al. |
| 7,750,050 B2 | 7/2010 | Schuchman et al. |
| 9,289,472 B2 | 3/2016 | Jensen et al. |
| 9,662,375 B2 | 5/2017 | Jensen et al. |
| 9,884,058 B2 | 2/2018 | Jensen et al. |
| 10,543,204 B2 | 1/2020 | Jensen et al. |
| 2001/0034042 A1 | 10/2001 | Srivastava |
| 2002/0006410 A1 | 1/2002 | Lukacs et al. |
| 2002/0035072 A1 | 3/2002 | Fan et al. |
| 2002/0037290 A1 | 3/2002 | Armen |
| 2002/0039583 A1 | 4/2002 | Subjeck et al. |
| 2002/0095135 A1 | 7/2002 | Meeker et al. |
| 2002/0119163 A1 | 8/2002 | Srikumaran |
| 2002/0127219 A1 | 9/2002 | Okkels et al. |
| 2002/0127718 A1 | 9/2002 | Kuppner et al. |
| 2002/0156250 A1 | 10/2002 | Wallen et al. |
| 2002/0172682 A1 | 11/2002 | Srivastava |
| 2002/0192230 A1 | 12/2002 | Srivastava |
| 2003/0012794 A1 | 1/2003 | Srivastava et al. |
| 2003/0035808 A1 | 2/2003 | Srivastava |
| 2003/0073094 A1 | 4/2003 | Young et al. |
| 2003/0129196 A1 | 7/2003 | Srivastava |
| 2003/0203846 A1 | 10/2003 | Srivastava et al. |
| 2003/0216315 A1 | 11/2003 | Nicchitta et al. |
| 2003/0236300 A1 | 12/2003 | Caplan et al. |
| 2004/0022796 A1 | 2/2004 | Srivastava |
| 2004/0047876 A1 | 3/2004 | Srivastava |
| 2005/0048608 A1 | 3/2005 | Chan et al. |
| 2005/0112640 A1 | 5/2005 | Davidson et al. |
| 2005/0153906 A1 | 7/2005 | Bedwell et al. |
| 2005/0202044 A1 | 9/2005 | Mizzen et al. |
| 2005/0267020 A1 | 12/2005 | Faure et al. |
| 2006/0009520 A1 | 1/2006 | Tall et al. |
| 2006/0089302 A1 | 4/2006 | Abulafia-Lapid et al. |
| 2006/0093612 A1 | 5/2006 | Srivastava |
| 2006/0264609 A1 | 11/2006 | Lehner et al. |
| 2006/0270833 A1 | 11/2006 | Henot et al. |
| 2007/0231337 A1 | 10/2007 | Multhoff |
| 2008/0009516 A1 | 1/2008 | Wustman |
| 2008/0014191 A1 | 1/2008 | Balch et al. |
| 2008/0019915 A1 | 1/2008 | Hadida-Ruah et al. |
| 2008/0026012 A1 | 1/2008 | Podack et al. |
| 2008/0039400 A1 | 2/2008 | Van Eden et al. |
| 2008/0039497 A1 | 2/2008 | Greensmith et al. |
| 2008/0132450 A1 | 6/2008 | Lee et al. |
| 2008/0161258 A1 | 7/2008 | Henning et al. |
| 2008/0305084 A1 | 12/2008 | Podsakoff et al. |
| 2009/0163500 A1 | 6/2009 | Lingwood et al. |
| 2009/0203065 A1 | 8/2009 | Gehman et al. |
| 2009/0203605 A1 | 8/2009 | Segatori et al. |
| 2009/0208524 A1 | 8/2009 | Srivastava et al. |
| 2009/0227572 A1 | 9/2009 | Barber et al. |
| 2009/0298857 A1 | 12/2009 | Chiosis et al. |
| 2009/0318343 A1 | 12/2009 | Garigapati et al. |
| 2010/0004277 A1 | 1/2010 | Bulawa et al. |
| 2010/0087490 A1 | 4/2010 | Young |
| 2010/0130730 A1 | 5/2010 | Garigapati et al. |
| 2010/0168016 A1 | 7/2010 | Ackerman et al. |
| 2010/0196279 A1 | 8/2010 | Lockhart |
| 2010/0221225 A1 | 9/2010 | Byrne et al. |
| 2010/0266571 A1 | 10/2010 | Lockhart et al. |
| 2010/0317690 A1 | 12/2010 | Kawamura et al. |
| 2010/0329985 A1 | 12/2010 | Van Eden et al. |
| 2011/0027254 A1 | 2/2011 | Daniel et al. |
| 2011/0028403 A1 | 2/2011 | Le Poole et al. |
| 2011/0081428 A1 | 4/2011 | Lithgow et al. |
| 2011/0105560 A1 | 5/2011 | Wustman |
| 2011/0110938 A1 | 5/2011 | Chiu et al. |
| 2011/0123512 A1 | 5/2011 | Prahlad et al. |
| 2011/0286993 A1 | 11/2011 | Jensen et al. |
| 2012/0115908 A1 | 5/2012 | Greensmith et al. |
| 2013/0230506 A1 | 9/2013 | Jensen et al. |
| 2014/0080769 A1 | 3/2014 | Platt et al. |
| 2015/0004151 A1 | 1/2015 | Jensen et al. |
| 2015/0126551 A1* | 5/2015 | Greensmith ........ A61K 31/4545 514/318 |
| 2015/0284472 A1 | 10/2015 | Sard et al. |
| 2015/0284475 A1 | 10/2015 | Sardi et al. |
| 2020/0113888 A1 | 4/2020 | Jensen et al. |
| 2020/0121668 A1 | 4/2020 | Jensen et al. |

FOREIGN PATENT DOCUMENTS

| | | |
|---|---|---|
| EP | 2318032 | 4/2012 |
| EP | 2484371 | 8/2012 |
| EP | 2659904 A1 | 11/2013 |
| EP | 2481400 B1 | 6/2014 |
| WO | WO 1989/08661 A1 | 9/1989 |
| WO | WO-1997016439 | 5/1997 |
| WO | WO-2000/35914 A1 | 6/2000 |
| WO | WO-2000050403 | 8/2000 |
| WO | WO-200117554 | 3/2001 |
| WO | WO-200134184 | 5/2001 |
| WO | WO-200152877 | 7/2001 |
| WO | WO-200152890 | 7/2001 |
| WO | WO-200234777 | 5/2002 |
| WO | WO 2002/065989 A2 | 8/2002 |
| WO | WO 2003/029288 A2 | 4/2003 |
| WO | WO-2003026653 A1 | 4/2003 |
| WO | WO-2003049692 | 6/2003 |
| WO | WO-2003/061684 | 7/2003 |
| WO | WO-2003/061684 A2 | 7/2003 |
| WO | WO-2003086452 | 10/2003 |
| WO | WO 2004/007539 A2 | 1/2004 |
| WO | WO-2005/041965 A1 | 5/2005 |
| WO | WO-2005120558 | 12/2005 |
| WO | WO-2007041285 | 4/2007 |
| WO | WO-2007/150064 | 12/2007 |
| WO | WO-2008021210 | 2/2008 |
| WO | WO 2008/039514 A1 | 4/2008 |
| WO | WO 2008/070010 A2 | 6/2008 |
| WO | WO-2008112525 | 9/2008 |
| WO | WO-2008117026 | 10/2008 |
| WO | WO-2009095452 | 8/2009 |
| WO | WO-2009100037 | 8/2009 |
| WO | WO-2009137721 | 11/2009 |
| WO | WO-2009137796 | 11/2009 |
| WO | WO-2009141627 | 11/2009 |
| WO | WO-2009/155936 A1 | 12/2009 |
| WO | WO-2009155936 | 12/2009 |
| WO | WO-2010015816 | 2/2010 |
| WO | WO-2010022461 | 3/2010 |
| WO | WO-2010053655 | 5/2010 |
| WO | WO-2010086418 | 8/2010 |
| WO | WO-2010092112 | 8/2010 |
| WO | WO-2010102988 | 9/2010 |
| WO | WO-2010116141 | 10/2010 |
| WO | WO-2010148253 | 12/2010 |
| WO | WO-2011019763 | 2/2011 |
| WO | WO-2011075686 | 6/2011 |
| WO | WO-2012/012656 A2 | 1/2012 |
| WO | WO-2012/072082 A1 | 6/2012 |
| WO | WO-2013/006076 A1 | 1/2013 |

(56) References Cited

FOREIGN PATENT DOCUMENTS

| WO | WO-2013/148333 A1 | 10/2013 |
|----|-------------------|---------|
| WO | WO-2014/071282 A1 | 5/2014  |
| WO | WO-2016/041561 A1 | 3/2016  |

OTHER PUBLICATIONS

Liscic, R., Molecular basis of ALS and FTD: implications for translational studies, Arhiv za Hihijenu Rada i Toksikologiju,, 66: 285-290, Dec. 1, 2015.

Rademakers et al., The Role of Tau (MAPT) in Frontotemporal Dementia and Related Tauopathies. Human Mutation, 24:277-295, 2004.

Götzl, J. et al., Impaired Protein Degradation in FTLD and Related Disorders, Aging Res Rev. Dec; 32:122-139, 2016.

Malik, B. et al., Co-induction of the heat shock response ameliorates disease progression in a mouse model of human spinal and bulbar muscular atrophy: implications for therapy, Brain, 136:926-43, 2013.

Custer, S. et al., Transgenic Mice Expressing Mutant Forms VCP/p97 Recapitulate the Full Spectrum of IBMPFD Including Degeneration in Muscle, Brain and Bone, Hum Mol Genet. 1;19(9):1741-55, 2010.

Ahmed, M. et al., Targeting Protein Homeostasis in Sporadic Inclusion Body Myositis, Sci. Tran Med; 8(331), Mar. 2016.

Ratti, A. et al., Physiological Functions and Pathobiology of TDP-43 and FUS/TLS Proteins, J Neurochem;138 Suppl 1:95-111, Aug. 2016.

Li, Q. et al., The cleavage pattern of TDP-43 determines its rate of clearance and cytotoxicity, Nature Communications 6; 6183, 2015.

Yoshiyama, Y. et al ., Frontotemporal Dementia and Tauopathy, Curr Neurol Neurosci Rep.; 1(5):413-21, Sep. 2001.

Tanida, I. et al., LC3 and Autophagy, Methods Mol Biol, 445, 77-88, 2008.

Lee, E. et al., Gains or losses: molecular mechanisms of TDP43-mediated neurodegeneration, Nat Rev Neurosci, 1: 38-50, Nov. 30, 2011.

Tresse, E., et al., VCP/p97 is essential for maturation of ubiquitin-containing autophagosomes and this function is impaired by mutations that cause IBMPFD, Autophagy, 6: 217-227, 2010.

Higuchi, M. et al., Axonal Degeneration Induced by Targeted Expression of Mutant Human Tau in Oligodendrocytes of Transgenic Mice That Model Glial Tauopathies, J Neurosci., 25 (41): 9434-9443, Oct. 2005.

Jeong, H. et al., Brain Inflammation and Microglia: Facts and Misconceptions, Exp Neurobiol., 22(2): 59-67, Jun. 2013.

Monahan, Z. et al., Stress granules at the intersection of autophagy and ALS, Brain Res.1649(Pt B): 189-200, Oct. 15, 2016.

Ito, D. et al., RNA Binding Proteins and the Pathological Cascade in ALS/FTD Neurodegeneration, Sci Transl Med., 9(415): eeah5436, 2017.

Alberti, S. et al.,Granulostasis: Protein Quality Control of RNP Granules, Front. Mol. Neurosci., 10:84, Mar. 27, 2017.

Fog, C. et al., The heat shock protein amplifier arimoclomol improves refolding, maturation and lysosomal activity of glucocerebrosidase, EBioMedicine, https://doi.org/10.1016/j.ebiom.2018.11.037.

Balogh et al.; The hyperfluidization of mammalian cell membranes acts as a signal to initiate the heat shock protein response. FEBS Journal 272 (2005) 6077-6086.

Botzler et al.; Synergistic effects of heat and ET-18-OCH3 on membrane expression of hsp70 and lysis of leukemic K562 cells. Experimental Hematology 27 (1999) 470-478.

Brunk et al.: Lysosomal involvement in apoptosis. Redox Rep. 2001; 6(2):91-7.

Brunk et al.: Photo-oxidative disruption of lysosomal membranes causes apoptosis of cultured human fibroblasts. Free Radical Biology & Medicine, vol. 23, No. 4, pp. 616-626, 1997.

Chung et al.; HSP72 protects against obesity-induced insulin resistance. PNAS Feb. 5, 2008 vol. 105, No. 5, 1739-1744.

Daugaard et al., "The heat shock protein 70 family: Highly homologous proteins with overlapping and distinct functions," Febs Letters, Elsevier, Amsterdam, vol. 581, No. 19, Jul. 31, 2007, pp. 3702-3710.

Ferlinz et al.; Stimulation of lysosomal sphingomyelin degradation by sphingolipid activator proteins. Chemistry and Physics of Lipids 102 (1999) 35-43.

Fleshner & Johnson: Endogenous extra-cellular heat shock protein 72: Releasing signal(s) and function. Int. J. Hyperthermia, Aug. 2005; 21(5):457-471.

Gehrmann et al.; Differential Up-Regulation of Cytosolic and Membrane-Bound Heat Shock Protein 70 in Tumor Cells by Anti-Inflammatory Drugs. Clinical Cancer Research vol. 10, 3354-3364, May 15, 2004.

Gehrmann et al.; Effects of Antineoplastic Agents on Cytoplasmic and Membrane-Bound Heat Shock Protein 70 (Hsp70) Levels. Biol. Chem., vol. 383, pp. 1715-1725, Nov. 2002.

Gehrmann et al.; The therapeutic implications of clinically applied modifiers of heat shock protein 70 (Hsp70) expression by tumor cells. Cell Stress and Chaperones (2008) 13: 1-10.

Harada et al.: Heat shock proteins and the antitumor T cell response. Biotherapy 10: 229-235, 1998.

Kalmar & Greensmith; Activation of the heath shock response in a primary cellular model of motoneuron neurodegeneration—evidence for neuroprotective and neurotoxic effects. Cellular & Molecular Biology Letters vol. 14 (2009) pp. 319-335.

Kalmar et al.; Late stage treatment with arimoclomol delays disease progression and prevents protein aggregation in the SOC1G93A mouse model of ALS. Journal of Neurochemistry 2008, 107, 339-350.

Kalmar et al.; Upregulation of Heat Shock Proteins Rescues Motoneurons from Axotomy-Induced Cell Death in Neonatal Rats. Experimental Neurology 176, 87-97 (2002).

Kieran et al., Treatment with arimoclomol, a coinducer of heat shock proteins, delays disease progression in ALS mice, Nature Medicine, 10(4): 402-45, Apr. 2004.

Kirkegaard et al., Hsp70 stabilizes lysosomes and reverts Niemann-Pick disease-associated lysosomal pathology, Nature Letters, 463: 549-554, Jan. 28, 2010.

Kirkegaard-Sorenson; Hsp70 binding to BMP—A novel mechanism for cellular protection. Dep. of Apoptosis, Danish Cancer Society, Feb. 2008. PhD Thesis. University of Copenhagen, Faculty of Health Sciences.

Kobayashi et al.: A lipid associated with the antiphospholipid syndrome regulates endosome structure and function. Nature Letters, vol. 392 Mar. 12, 1998.

Kolzer et al.: Interactions of acid sphingomyelinase and lipid bilayers in the presence of the tricyclic antidepressant desipramine. FEBS Letters 559 (2004) 96-98.

Nylandsted et al.: Heat shock protein 70 promotes cell survival by inhibiting lysosomal membrane permeabilization. J. Exp. Med. vol. 200, No. 4, Aug. 16, 2004 425-435.

Ohtsuka et al.; Inducers and co-inducers of molecular chaperones. Int. J. Hyperthermia, Dec. 2005; 21(8): 703-711.

Sambrook et al., Molecular Cloning, A Laboratory Manual, Cold Spring Harbor, Laboratory Press (1998), 1.101-1.104.

Tavaria et al.: A hitchhiker's guide to the human Hsp70 family. Mini-review. Cell stress & Chaperones (1996) 1 (1), 23-28.

Tidwell et al.: Administration of Hsp70 in vivo inhibits motor and sensory neuron degeneration. Cell Stress & Chaperones (2004) 9(1), 88-98.

Tytell & Hooper; Heat Shock proteins: new keys to the development of cytoprotective therapies. Expert Opin Ther Targets, Apr. 2001;5(2):267-87.

Tytell: Release of heat shock proteins (Hsps) and the effects of extracellular Hsps on neural cells and tissues. Int J Hypothermia, Aug. 2005; 21(5): 445-455.

Torok et al.; Heat shock protein coinducers with no effect on protein denaturation specifically modulate the membrane lipid phase. PNAS Mar. 18, 2003, vol. 100, No. 6, 3131-3136.

(56) References Cited

OTHER PUBLICATIONS

Vigh et al., Bimoclomol: A nontoxic, hydroxylamine derivative with stress protein-inducing activity and cytoprotective effects, *Nature Medicine*, 3(10): 1150-54, Oct. 1997.
Vigh et al.; Can the stress protein response be controlled by membrane-lipid therapy? Trends in Biochemical Sciences vol. 32 No. 8 (2007).
Wei et al.: Inhibition of proliferation and induction of apoptosis by abrogation of heat-shock protein (HSP) 70 expression in tumor cells. Cancer Immunol. Immunother. (1995) 40:73-78.
Yu et al.: Retinal uptake of intravitreally injected Hsc/Hsp70 and its effects on susceptibility to light damage. Molecular Vision 2001; 7:48-56.
Communication Pursuant to Article 94(3) EPC for Application No. 09768858.4 dated Jul. 26, 2011.
Du, W. et al., Cell Growth Inhibition by Farnseyltransferase Inhibitors is Mediated by Gain of Geranylgeranylated RhoB, *Molecular and Cellular Biology*, 19(3): 1831-40, Mar. 1999.
Prendergast, G. et al., Farnesyltransferase Inhibition Causes Morphological Reversion of ras-Transformed Cells by a Complex Mechanism that Involves Regulation of the Actin Cytoskeleton, *Molecular and Cellular Biology*, 14(6): 4193-4202, Jun. 1994.
Balabanov, S. et al., Quantitative proteomics analysis of BMS-214662 effects on CD34 positive cells from chronic myeloid leukaemia patients, *Proteomics*, 13: 153-68, 2013.
Mazieres, J. et al., Perspectives on farnesyl transferase inhibitors in cancer therapy, *Cancer Letters*, 206: 159-67, 2004.
Porcu, G. et al., A yeast-based genomic strategy highlights the cell protein networks altered by FTase inhibitor peptidomimetics, *Molecular Cancer*, 9: 197, 2010.
Horvath, I. et al., Membrane-associated stress proteins: More than simply chaperones, *Biochimica et Biophysica Acta*, 1778: 1653-64, 2008.
Simons, K. et al., Jamming the Endosomal System: Lipid Rafts and Lysosomal Storage Diseases, *Trends in Cell Biology*, 10: 459-62, 2000.
Goni, F. et al., Sphingomyelinases: enzymology and membrane activity, *Federation of European Biochemical Societies*, 531: 38-46, 2002.
Yenari, M. et al., The neuroprotective potential of heat shock protein 70 (HSP70), *Molecular Medicine Today*, 5: 525-31, 1999.
Keeling et al., Gentamicin-mediated suppression of Hurler syndrome stop mutations restores a low level of alpha-L-iduronidase activity and reduces lysosomal glycosaminoglycan accumulation, *Human Molecular Genetics*, 10: 291-99, 2001.
Meikle et al., Effect of lysosomal storage on bis(monoacylglycero)phosphate, *Biochem J.*, 411: 71-78, 2008.
Voellmy et al., Isolation and functional analysis of a human 70,000-dalton heat shock protein gene segment, Proc. Natl. Acad. Sci. USA, 82: 4949-53, 1985.
Wu, et al., Structure and expression of the human gene ancoding major heat shock protein HSP70, Mol. Cell. Biol., 5(2): 330-41, 1985.
Winchester, B. et al., The molecular basis of lysosomal storage disease, *Biochemical Society Transactions*, 28: 150-54, 2000.
Au, Q. et al., High-content image-based screening for small-molecule chaperone amplifiers in heat shock, *Journal of Biomolecular Screening*, 13(19): 953-959, 2008.
Bruening, W. et al., Up-regulation of protein chaperones preserves viability of cells expressing toxic Cu/Zn-superoxide dismutase mutants associated with amyotrophic lateral sclerosis, *Journal of Neurochemistry*, 72: 693-99, 1999.
Horváth, I. et al., Cell biology: Stability in times of stress, *Nature*, 463(7280): 436-438, 2010.
Polakowski, J. et al., Bimoclomol elevates heat shock protein 70 and cytoprotects rat neonatal cardiomyocytes, *European Journal of Pharmacology*, 435: 73-77, 2002.
Hallows, J. et al., p35/p25 Is Not Essential for Tau and Cytoskeletal Pathology or Neuronal Loss in Niemann-Pick Type C Disease, The Journal of Neuroscience, 26: 2738-2744, 2006.

Parfitt, D. et al., The heat-shock response co-inducer arimoclomol protects against retinal degeneration in rhodopsin retinitis pigmentosa, *Cell Death and Disease*, 5: 1-10, 2014.
Patterson, M. et al., Miglustat for treatment of Niemann-Pick C disease: a randomised controlled study, Lancet Neurology, 6: 765-772, 2007.
Kabakov, A. et al., Pharmacological attenuation of apoptosis in reoxygenated endothelial cells, *Cellular and Molecular Life Sciences*, 61: 3076-86, 2004.
Cohen, F. et al., Therapeutic approaches to protein-misfolding diseases, *Nature*, 426:905-909, 2003.
Freeman, B. et al., The human cytosolic molecular chaperones hsp90 (hsc70) and hdj-1 have distinct roles in recognition of a non-native protein and protein refolding, *The European Molecular Biology Journal*, 15: 2969-79, 1996.
Kirkegaard-Sorenson et al.; Interaction between Hsp70 and bis(monoacylglycero)phosphate stabilizes lysosomes and promotes cell survival. APMIS, 116( 5): 436-437, 2008.
Ng et al., Predicting deleterious amino acid substitutions. Genome Res. 2001 11: 863-874.
Zhu Yunxiang et al. "Dexmethasone-mediated up-regulation of the mannose receptor improves the delivery of recombinant glucocerebrosidase to Gaucher macrophages," The Journal of Pharmacology and Experimental Therapeutics, Feb. 2004, vol. 308, No. 2, pp. 705-711.
Jaatela, M. et al., Emerging Role of Heat Shock Proteins in Biology and Medicine, *Annals of Medicine*, 24: 249-258, 1992.
Hu, W. et al., Proteomic identification of heat shock protein 70 as a candidate target for enhancing apoptosis induced by farnesyl transferase inhibitor, *Proteomics*, 3: 1904-11, 2003.
Kalmar, B. et al., The effect of treatment with BRX-220, a co-inducer of heat shock proteins, on sensory fibers of the rat following peripheral nerve injury, *Exp. Neurol.*, 184: 636-647, 2003.
Rakonczay, Z. et al., Nontoxic heat shock protein coinducer BRX-220 protects against acute pancreatitis in rats, *Free Radical Biology and Medicine*, 32(12): 1283-1292, 2002.
Lubbers, N. et al., Oral bimoclomol elevates heat shock protein 70 and reduces myocardial infarct size in rats, *European Journal of Pharmacology*, 435: 79-83, 2002.
Cudkowicz, M. et al., Arimoclomol at Dosages up to 300 Mg/day is Well Tolerated and Safe in Amyotrophic Lateral Sclerosis, *Muscle & Nerve*, pp. 837-844, Jul. 2008.
Lepist, E. et al., Contribution of the organic anion transporter OAT2 to the renal active tubular secretion of creatinine and mechanism for serum creatinine elevations caused by cobicistat, *Kidney International*, 86: 350-357, 2014.
Roth, A. et al., Interaction between Hsp70 and bis(monoacylglycero)phosphate stabilizes lysosomes and promotes cell survival, APMIS, 116: 437, 2008.
Balwani, M. et al., Gaucher disease: When molecular testing and clinical presentation disagree—the novel c.1226A.>G(p.N370S)-RecNcil allele, J Inherit Metab Dis, 34:789-793, 2011.
Bergamin, N. et al., A human neuronal model of Niemann Pick C disease developed from stem cells isolated from patient's skin, Orphanet Journal of Rare Diseases, 8(1): 34, 2013.
Bligh, E. et al., A Rapid Method of Total Lipid Extraction And Purification, Canadian Journal of Biochemistry and Physiology, 37(8): 911-917, 1959.
Blom, T. et al., FTY720 Stimulates 27-Hydroxycholesterol Production and Confers Atheroprotective Effects in Human Primary Macrophages, Circ. Res. 106: 720-729, 2010.
Boyum, A., Separation of white blood cells, Nature, 204: 793-794 1964.
Gan-Or. Z. et al., Differential effects of severe vs mild GBA mutations on Parkinson disease, Neurology, 84: 880-887, Mar. 3, 2015.
Ingemann, L. et al., Lysosomal storage diseases and the heat shock response: convergences and therapeutic opportunities, Journal of Lipid Research, 55: 2198-2210, May 16, 2014.
Mahalka, A. et al., Human heat shock protein 70 (Hsp70) as a peripheral membrane protein, Biochimica et Biophysica Acta, 1838: 1344-1361, Jan. 28, 2014.

(56) References Cited

OTHER PUBLICATIONS

McNeill et al., Ambroxol improves lysosomal biochemistry in glucocerebrosidase mutation-linked Parkinson disease cells, Brain, 137: 1481-1495, Feb. 25, 2014.
Mu, T., et al., Chemical and biological approaches synergize to ameliorate protein-folding diseases, Cell, 134: 769-81, Sep. 5, 2008.
Sardi, S. et al., CNS expression of glucocerebrosidase corrects alpha-synuclein pathology and memory in a mouse model of Gaucher-related synucleinopathy, PNAS, 108(29): 12101-12106, Jul. 19, 2011.
Sardi, S. et al., Augmenting CNS glucocerebrosidase activity as a therapeutic strategy for parkinsonism and other Gaucher-related synucleinopathies, PNAS, 110(9): 3537-3542, Feb. 26, 2013.
Wang, S. et al., ABCA1 and nascent HDL biogenesis, Biofactors 40(6): 547-554, Nov. 2014.
Witte, M. et al., Ultrasensitive in situ visualization of active glucocerebrosidase molecules, Nature Chemical Biology, 6(12): 907-913, Oct. 31, 2010.
Xing, B. et al., Hsp70 plays an important role in high-fat diet induced gestational hyperglycemia in mice, J Physiol Biochem, 71: 649-658, Aug. 29, 2015.
Schapira, A., Glucocerebrosidase and Parkinson disease: Recent advances, Molecular and Cellular Neuroscience, 66:37-42, 2015.
Clark, L.N. et al. (2017) "Mutations in the glucocerebrosidase gene are associated with early-onset Parkinson disease" Neurology, 69(12): 1270-1277.
Senkevich, K.A. et al. (2016) "Glucocerebrosidase Activity in Patients Having Parkinson's Disease Associated with Mutations within *GBA* Gene" Medical Academic Journal, 16(4):65-66 (Russian, with English translation, 2 pages).
AdisInsight (2019) "Arimoclomol—Orphazyme" Springer [online]. Retrieved from: https://adisinsight.springer.com/drugs/800016664; retrieved on Jun. 14, 2019; 2 pages.
Haldimann, P. et al., "The novel hydroxylamine derivative NG-094 suppresses polyglutamine protein toxicity in Caenorhabditis elegans" J Biol Chem, May 27, 2011;286(21):18784-94. doi:10.1074/jbc.M111.234773. Epub Apr. 6, 2011 (Abstract, 2 pages).
Hargitai, J. et al., "Bimoclomol, a heat shock protein co-inducer, acts by the prolonged activation of heat shock factor-1" Biochem Biophys Res Commun., Aug. 1, 2003;307(3):689-695. doi: 10.1016/s0006-291x(03)01254-3 (Abstract, 2 pages).
Kalmar, B. et al., "The role of heat shock proteins in Amyotrophic Lateral Sclerosis: The therapeutic potential of Arimoclomol" Pharmacol Ther, Jan. 2014;141(1):40-54 (Abstract, 2 pages).
Kocsy, G. et al., "Glutathione reductase activity and chilling tolerance are induced by a hydroxylamine derivative BRX-156 in maize and soybean" Plant Sci, Apr. 2001;160(5):943-950. doi:10.1016/s0168-9452(01)00333-8 (Abstract, 1 page).
Literati-Nagy, Z. et al., "A novel insulin sensitizer drug candidate-BGP-15-can prevent metabolic side effects of atypical antipsychotics" Pathol Oncol Res, Oct. 2012;18(4):1071-6. doi: 10.1007/s12253-012-9546-4. Epub Jun. 30, 2012 (Abstract, 1 page).

\* cited by examiner

ARIMOCLOMOL FOR TREATING GLUCOCEREBROSIDASE ASSOCIATED DISORDERS

REFERENCE TO RELATED APPLICATIONS

This application is a continuation of U.S. patent application Ser. No. 16/092,070, filed Oct. 8, 2018, which is a 371 application of PCT/EP2017/060205, filed Apr. 28, 2017, which claims priority of Danish patent application No. PA201670281, filed Apr. 29, 2016. The entire content of each of these applications is incorporated herein by reference.

TECHNICAL FIELD

The present invention relates to an active pharmaceutical ingredient selected from N-[2-hydroxy-3-(1-piperidinyl)-propoxy]-pyridine-1-oxide-3-carboximidoyl chloride, its stereoisomers and the acid addition salts thereof (arimoclomol), for use in a method of treating a glucocerebrosidase (GBA)-associated disorder other than Gaucher's disease (GD), including GBA-associated alpha-synucleinopathies such as GBA-associated Parkinson's disease (PD), GBA-associated dementia with Lewi bodies (DLB) and GBA-associated multiple system atrophy (MSA).

BACKGROUND

Gaucher's disease (GD) is the most common of the lysosomal storage diseases characterized by an accumulation of glucocerebrosides. It is a form of sphingolipidosis as it involves dysfunctional metabolism of sphingolipids. To date, up to 300 mutations in the GBA gene are known and linked to Gaucher disease. GBA mutations can be categorized as mild (causing GD type I, nonneuronopathic) or severe (causing GD types II and III). Homozygous GBA mutations as well as compound heterozygous mutations cause GD. A few common mutations predominate, the most prevalent for GD Type I being a missense mutation resulting in the substitution of a serine for asparagine at amino acid residue 370 (N370S), and the most prevalent for Type II and III being L444P (Codons are numbered from the first codon of the mature protein i.e. without the signal peptide).

Many of these mutations are also found in patients with Parkinson's disease (PD).

Heterozygous mutations as found in GBA mutation carriers (having one mutated GBA gene) are found to predispose for development of Parkinson's disease (Gan-Or et al., Neurology, 2015). Mutations in GBA are now considered one of the main genetic risk factors for Parkinson's disease. It has been estimated that at least 8% of patients with Parkinson's disease have mutations in the GBA gene, both mild and severe GBA mutations, including L444P heterozygotes. Also secondary deficiencies of GBA activity may be linked to Parkinson's disease.

The primary pathology leading from GBA deficiency to Parkinson's disease is not clarified, but pre-clinical experiments suggest an inverse relationship to α-synuclein. Carriers of GBA gene mutations appear also to have an increased risk of developing dementia with Lewy bodies (DLB) and possibly multiple system atrophy (MSA), providing a link between GBA deficiency and at least some of the alpha-synucleinopathies.

WO 2014/071282 discloses a recombinant self-complementary adeno-associated viral vector encoding human glucocerebrosidase (AAV-GBAI) in models to support glucocerebrosidase augmentation therapies for PD and related synucleinopathies and tauopathies.

WO 2013/148333 discloses salicylic acid derivatives as glucocerebrosidase activators for treating Gaucher's disease and inhibiting the onset of Gaucher's disease symptoms in a patient having a GBA gene mutation and for treating Parkinson's disease.

WO 2009/155936 discloses heat shock protein 70 and inducers thereof for treating lysosomal storage diseases, including Gaucher's disease.

WO 2005/041965 discloses use of the heat shock inducer arimoclomol for protecting neurons in neurodegenerative diseases, including Parkinson's disease.

SUMMARY

Arimoclomol is a heat shock protein amplifier currently under evaluation in the treatment of paediatric lysosomal storage disorders and amyotrophic lateral sclerosis (ALS).

The present inventors have now found that arimoclomol increases GBA levels and increases GBA activity, not only in GBA homozygotes (presenting with Gaucher's disease and markedly reduced GBA activity), but also in mutant GBA heterozygotes (carriers). Specifically, arimoclomol increases GBA activity in GBA homozygotes (Gaucher patient) to clinically unaffected activity level. Furthermore, arimoclomol increases GBA activity in GBA heterozygotes (clinically unaffected), and increases GBA enzyme amount (total level and matured/post-ER GBA).

The present inventors also show herein that arimoclomol increases GBA activity in Parkinson's disease patients with mutated GBA alleles (heterozygous or homozygous, clinically unaffected re Gaucher's disease).

It is an aspect to provide an active pharmaceutical ingredient selected from N-[2-hydroxy-3-(1-piperidinyl)-propoxy]-pyridine-1-oxide-3-carboximidoyl chloride (arimoclomol), its stereoisomers and the acid addition salts thereof, for use in a method of treating a glucocerebrosidase (GBA)-associated disorder.

In one embodiment said GBA-associated disorder is associated with reduced GBA enzyme levels and/or reduced GBA enzyme activity. In one embodiment said GBA-associated disorder is associated with one or more GBA gene mutations, including heterozygous and homozygous GBA gene mutations.

In one embodiment said GBA-associated disorder is a GBA-associated alpha-synucleinopathy, such as selected from the group consisting of GBA-associated Parkinson's disease (PD), GBA-associated dementia with Lewi bodies (DLB) and GBA-associated multiple system atrophy (MSA).

In one embodiment said GBA-associated Parkinson's disease is associated with a genetically high-risk Parkinson's disease GBA genotype.

Also provided is an active pharmaceutical ingredient selected from N-[2-hydroxy-3-(1-piperidinyl)-propoxy]-pyridine-1-oxide-3-carboximidoyl chloride, its stereoisomers and the acid addition salts thereof, for use in a method of increasing GBA levels and/or GBA activity.

DETAILED DESCRIPTION

Figure 1:
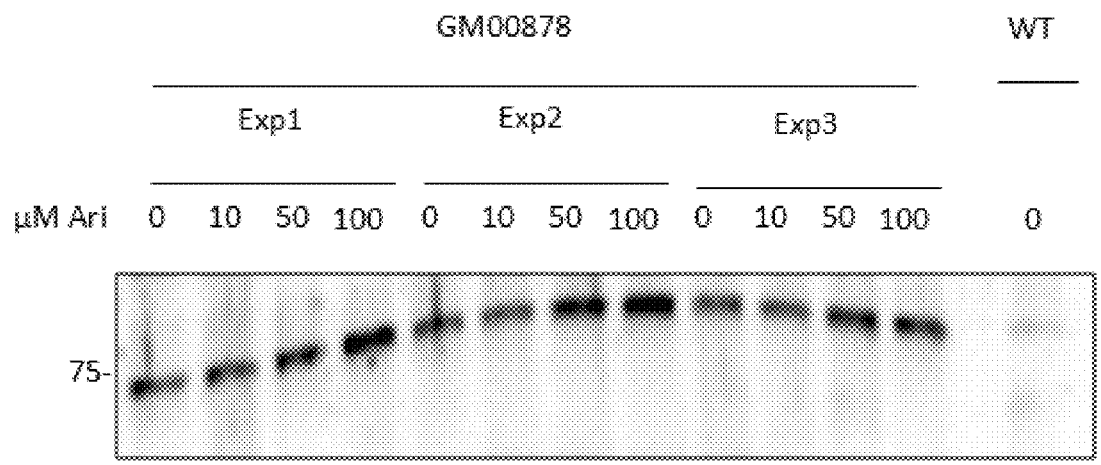
FIG. 1: Arimoclomol-induced dose-dependent increase in ER Hsp70 (BiP) in primary cells (human fibroblasts) from individual with a heterozygous GBA allele containing the L444P,A456P,V460V mutations in cis (carrier, clinically unaffected re. Gaucher's disease). See Example 1.
Figure 2:
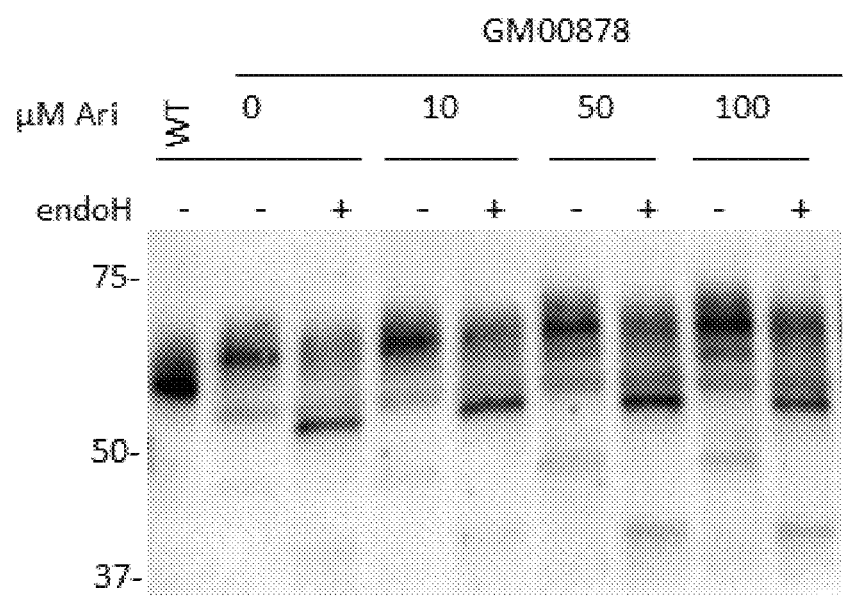
FIG. 2: Arimoclomol-induced dose-dependent increase in GBA enzyme amount in primary cells (human fibroblasts) from individual with a heterozygous GBA allele containing the L444P,A456P,V460V mutations in cis (carrier, not affected with Gaucher's disease). See Example 1.

Beta-glucocerebrosidase or glucocerebrosidase (UniProt entry P04062, GLCM_HUMAN, also called glucosylceramidase, acid beta-glucosidase, D-glucosyl-N-acylsphingosine glucohydrolase, GCase or GBA) is an enzyme with glucosylceramidase activity that cleaves, by hydrolysis, the beta-glucosidic linkage of glucocerebroside, an intermediate in glycolipid metabolism:

$$\text{D-glucosyl-N-acylsphingosine} + H_2O = \text{D-glucose} + \text{N-acylsphingosine}.$$

GBA requires saposin C and anionic phospholipids for activity. It is localized in the lysosome. It is encoded by the GBA gene (official name: glucosidase, beta, acid; Gene/Locus MIM number 606463; EC 3.2.1.45). Alternative splicing results in multiple transcript variants.

Mutations in the GBA gene, which encodes the lysosomal enzyme that is deficient in Gaucher's disease, are important and common risk factors for Parkinson's disease and related disorders. This association was first recognised in the clinic, where parkinsonism was noted, albeit rarely, in patients with Gaucher's disease and more frequently in relatives who were obligate carriers (an individual who may be clinically unaffected but who must carry a gene mutation based on analysis of the family history).

GBA gene mutations are continuously updated in the LOVD CCHMC Molecular Genetics Laboratory Mutation Database, Gaucher Disease; glucosidase, beta, acid (GBA) at 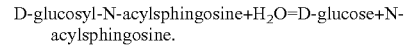 https://research.cchmc.org/LOVD2/home.php?select_db=GBA.

Subsequently, findings from large studies showed that patients with Parkinson's disease and associated Lewy body disorders had an increased frequency of GBA mutations when compared with control individuals. Patients with GBA-associated parkinsonism exhibit varying parkinsonian phenotypes but tend to have an earlier age of onset and more associated cognitive changes than patients with parkinsonism without GBA mutations. Hypotheses proposed to explain this association include a gain-of-function due to mutations in glucocerebrosidase that promotes α-synuclein aggregation; substrate accumulation due to enzymatic loss-of-function, which affects α-synuclein processing and clearance; and a bidirectional feedback loop.

Alpha-synuclein is a synuclein protein of unknown function primarily found in neural tissue. It can aggregate to form insoluble fibrils in pathological conditions characterized by Lewy bodies, such as Parkinson's disease, dementia with Lewy bodies, and multiple system atrophy. Alpha-synuclein is the primary structural component of Lewy body fibrils.

Arimoclomol is a small-molecule inducer of the heat shock proteins including Hsp70. It is currently being investigated for treatment of amyotrophic lateral sclerosis (ALS) and the lysosomal storage disorder Niemann-Pick disease type C. Induction of the heat shock proteins including Hsp70 protects lysosomal membranes and increases activity of lysosomal enzymes responsible for degradation of lysosomal substrate.

The present inventors show herein that arimoclomol increases GBA activity in cells from a patient with Gaucher's disease type III (e.g. L444P/L444P) to clinically unaffected activity levels (in some instances same levels as GBA mutation carriers). Also shown herein is that arimoclomol surprisingly increases GBA activity in cells from a GBA mutation carrier (e.g. L444P heterozygous) more than 2-fold of clinically unaffected activity levels. Furthermore, arimoclomol increases N370S GBA activity in cells from a PD patient. Thus, GBA activity—and levels—can be increased also in cells from mutant GBA heterozygotes (carriers), and in cells from mutant GBA homozygotes who are clinically unaffected re Gaucher's disease.

Arimoclomol-induced increase in GBA levels and/or activity may thus provide useful for treating a range of proteinopathic disorders wherein GBA levels and/or activity is compromised.

Arimoclomol is defined herein as an active pharmaceutical ingredient selected from N-[2-hydroxy-3-(1-piperidinyl)-propoxy]-pyridine-1-oxide-3-carboximidoyl chloride, its stereoisomers and the acid addition salts thereof.

Provided herewith is arimoclomol for use in the treatment of GBA deficiencies. In one embodiment said GBA deficiency does not include Gaucher's disease (GD) per se/as such.

Provided herewith is arimoclomol for use in the treatment of a glucocerebrosidase (GBA)-associated disorder other than Gaucher's disease (GD).

In one embodiment said treatment is prophylactic, curative or ameliorating. In one particular embodiment, said treatment is prophylactic. In another embodiment, said treatment is curative. In a further embodiment, said treatment is ameliorating.

Also provided herewith is use of arimoclomol for the manufacture of a medicament for the treatment of a glucocerebrosidase (GBA)-associated disorder other than Gaucher's disease (GD).

Also provided herewith is a method of treating a glucocerebrosidase (GBA)-associated disorder other than Gaucher's disease (GD), said method comprising administering an effective amount of arimoclomol to an individual in need thereof.

The term "Individual" or "subject" refers to vertebrates, in particular a member of a mammalian species, preferably primates including humans. In a preferred embodiment, an individual as used herein is a human being, male or female, of any age.

An "individual in need thereof" refers to an individual who may benefit from the present invention. In one embodiment, said individual in need thereof is a diseased individual, wherein said disease is a GBA-associated disorder.

GBA-Associated Disorders

In one embodiment there is provided a compound selected from the group consisting of (+)-R—N-[2-hydroxy-3-(1-piperidinyl)-propoxy]-pyridine-1-oxide-3-carboximidoyl chloride citrate; (−)-S—N-[2-hydroxy-3-(1-piperidinyl)-propoxy]-pyridine-1-oxide-3-carboximidoyl chloride citrate; (+)-R—N-[2-hydroxy-3-(1-piperidinyl)-propoxy]-pyridine-1-oxide-3-carboximidoyl chloride maleate; and (−)-S—N-[2-hydroxy-3-(1-piperidinyl)-propoxy]-pyridine-1-oxide-3-carboximidoyl chloride maleate, for use in the treatment of a GBA-associated disorder.

Reference to arimoclomol, as defined herein, for use in the treatment of a GBA-associated disorder encompasses any one of the below conditions.

A GBA-associated disorder as defined herein may refer to any disorder which has an association with GBA levels and/or GBA activity. Thus, reduced levels and/or reduced activity of GBA is associated with a GBA-associated disorder as defined herein. Associated with in one embodiment means predisposes for (or increases risk of developing; or presenting with).

In one embodiment the GBA-associated disorder is not Gaucher's disease. In one embodiment the GBA-associated disorder is not Gaucher's disease type I. In one embodiment the GBA-associated disorder is not Gaucher's disease type II. In one embodiment the GBA-associated disorder is not Gaucher's disease type III. In one embodiment the GBA-associated disorder is not Gaucher's disease types II or III.

In one embodiment the GBA-associated disorder is associated with reduced GBA enzyme levels.

In one embodiment the GBA-associated disorder is associated with reduced GBA enzyme activity.

Reduced GBA enzyme levels and/or GBA activity may also be defined as impaired GBA enzyme levels and/or GBA activity; insufficient GBA enzyme levels and/or GBA activity; or deficient GBA enzyme levels and/or GBA activity.

In one embodiment the GBA-associated disorder is referred to as a GBA-deficiency.

In one embodiment the GBA-associated disorder has a GBA activity and/or enzyme level which is reduced yet sufficient to remain clinically unaffected with respect to Gaucher's disease (i.e. does not have and is not diagnosed with Gaucher's disease). In one embodiment the GBA-associated disorder has a GBA activity and/or enzyme level which is reduced compared to wild type activity levels.

In one embodiment the GBA-associated disorder is associated with one or more individual GBA gene mutations. In one embodiment the GBA-associated disorder is an individual having one or more GBA gene mutations who remain clinically unaffected re Gaucher's disease.

In one embodiment the GBA-associated disorder is associated with one or more mild GBA gene mutations (associated with GD type I; TI).

In another embodiment the GBA-associated disorder is associated with one or more severe GBA gene mutations (associated with GD type II; TII, and GD type III; TIII).

In one embodiment the GBA-associated disorder is associated with one or more heterozygous GBA gene mutations, wherein said heterozygous GBA gene mutations do not cause or result in the development of Gaucher's disease.

In one embodiment the GBA-associated disorder is an individual having one or more heterozygous GBA gene mutations who remain clinically unaffected re Gaucher's disease.

In one embodiment the GBA-associated disorder is associated with one or more homozygous GBA gene mutations and/or compound heterozygous GBA gene mutations, wherein said GBA gene mutations do not cause or result in the development of Gaucher's disease.

In one embodiment the GBA-associated disorder is an individual having one or more homozygous and/or compound heterozygous GBA gene mutations who remain clinically unaffected re Gaucher's disease.

Specific mutations in the GBA gene that may affect the activity of the GBA protein include L444P, D409H, D409V, E235A, E340A, E326K, N370S, N370S/1-BP ins 84G, V394L, A456P, V460V, C342G, G325R, P415R, Y133*, F213I, N188S and IVS2+1G>A/N188S.

In one embodiment, the GBA-associated disorder is associated with (or comprises, presents with) one or more mutations in the GBA gene selected from the group consisting of L444P, D409H, D409V, E235A, E340A, E326K, N370S, N370S/1-BP ins 84G, V394L, A456P, V460V, C342G, G325R, P415R Y133*, F213I, N188S and IVS2+1G>A/N188S. Said one or more mutations in the GBA gene can be heterozygous, compound heterozygous or homozygous mutations.

In one embodiment the GBA-associated disorder is an individual having one or more GBA gene mutations selected from the group consisting of L444P, D409H, D409V, E235A, E340A, E326K, N370S, N370S/1-BP ins 84G, V394L, A456P, V460V, C342G, G325R, P415R Y133*, F213I, N188S and IVS2+1G>A/N188S who remain clinically unaffected re Gaucher's disease. Said one or more mutations in the GBA gene can be heterozygous, compound heterozygous or homozygous mutations.

In one embodiment the GBA-associated disorder is associated with the L444P GBA gene mutation (L444P/, L444P/+ or L444P/L444P). A heterozygous GBA allele containing the L444P mutation may be referred to as L444P/+.

In one embodiment the GBA-associated disorder is associated with the D409H GBA gene mutation.

In one embodiment the GBA-associated disorder is associated with the D409V GBA gene mutation.

In one embodiment the GBA-associated disorder is associated with the E235A GBA gene mutation.

In one embodiment the GBA-associated disorder is associated with the E340A GBA gene mutation.

In one embodiment the GBA-associated disorder is associated with the E326K GBA gene mutation.

In one embodiment the GBA-associated disorder is associated with the N370S GBA gene mutation. A homozygous GBA allele containing the N370S mutation may be referred to as N370S/N370S. A heterozygous GBA allele containing the N370S mutation may be referred to as N370S/+.

In one embodiment the GBA-associated disorder is associated with the N370S/1-BP ins 84G GBA gene mutation.

In one embodiment the GBA-associated disorder is associated with the V394L GBA gene mutation.

In one embodiment the GBA-associated disorder is associated with the A456P GBA gene mutation.

In one embodiment the GBA-associated disorder is associated with the V460V GBA gene mutation.

In one embodiment the GBA-associated disorder is associated with the C342G GBA gene mutation.

In one embodiment the GBA-associated disorder is associated with the G325R GBA gene mutation.

In one embodiment the GBA-associated disorder is associated with the P415R GBA gene mutation.

In one embodiment the GBA-associated disorder is associated with the Y133* GBA gene mutation.

In one embodiment the GBA-associated disorder is associated with the F213I GBA gene mutation.

In one embodiment the GBA-associated disorder is associated with the N188S and/or IVS2+1G>A/N188S GBA gene mutation.

In one embodiment the GBA-associated disorder is associated with one or more GBA gene mutations without accompanying reduction in GBA enzyme activity.

In one embodiment the GBA-associated disorder is associated with reduced GBA enzyme activity and said GBA gene is wild-type. In one embodiment the GBA-associated disorder is associated with idiopathic reduced GBA enzyme activity.

A wild type GBA allele may be referred to as (+/+) (no GBA mutation).

In one embodiment the GBA-associated disorder is associated with reduced GBA activity due to suppression of activity of the protein.

In one embodiment the GBA-associated disorder is associated with reduced GBA activity due to repression of transcription or translation of the gene/protein.

In one embodiment the GBA-associated disorder is associated with reduced GBA activity and said GBA gene is wild-type, and the reduction in GBA activity is due to suppression of activity of the protein and/or repression of transcription or translation of the gene/protein.

In one embodiment the GBA-associated disorder is an individual with a heterozygous GBA allele containing one or more mutations selected from the group consisting of L444P, D409H, D409V, E235A, E340A, E326K, N370S, N370S/1-BP ins 84G, V394L, A456P, V460V, C342G, G325R, P415R, Y133*, F213I, N188S and IVS2+1G>A/N188S.

In one embodiment the GBA-associated disorder is an individual with a heterozygous GBA allele containing the L444P,A456P,V460V mutations in cis.

In one embodiment the GBA-associated disorder is a L444P,A456P,V460V Heterozygote.

In one embodiment the GBA-associated disorder is heterozygous for the complex GBA allele L444P,A456P, V460V.

In one embodiment the GBA-associated disorder is a GBA mutation carrier. In one embodiment the GBA-associated disorder is an obligate carrier. In one embodiment the GBA mutation carrier is clinically unaffected re. Gaucher's disease.

In one embodiment the GBA-associated disorder is a clinically unaffected grand-parent, parent, sibling or child of a Gaucher's disease patient.

In one embodiment the GBA-associated disorder is a clinically unaffected parent or sibling of a Gaucher's disease patient.

In one embodiment the GBA-associated disorder is an individual with a homozygous or compound heterozygous GBA allele containing one or more mutations selected from the group consisting of L444P, D409H, D409V, E235A, E340A, E326K, N370S, N370S/1-BP ins 84G, V394L, A456P, V460V, C342G, G325R, P415R, Y133*, F213I, N188S and IVS2+1G>A/N188S, wherein said individual remain clinically unaffected re Gaucher's disease.

In one embodiment the GBA-associated disorder is an individual with a homozygous GBA allele containing the N370S/N370S mutation.

In one embodiment there is provided an active pharmaceutical ingredient selected from N-[2-hydroxy-3-(1-piperidinyl)-propoxy]-pyridine-1-oxide-3-carboximidoyl chloride, its stereoisomers and the acid addition salts thereof, for use in a method of treating a glucocerebrosidase (GBA)-associated disorder, such as a glucocerebrosidase (GBA)-associated disorder other than Gaucher's disease (GD).

In one embodiment the glucocerebrosidase (GBA)-associated disorder is GBA-associated parkinsonism.

In one embodiment the GBA-associated disorder is a GBA-associated Lewy body disorder, such as a GBA-associated Lewy body disorder selected from the group consisting of GBA-associated Parkinson's disease, GBA-associated dementia with Lewy bodies, and GBA-associated multiple system atrophy.

In one embodiment there is provided an active pharmaceutical ingredient selected from N-[2-hydroxy-3-(1-piperidinyl)-propoxy]-pyridine-1-oxide-3-carboximidoyl chloride, its stereoisomers and the acid addition salts thereof, for use in a method of treating a GBA-associated alpha-synucleinopathy.

A GBA-associated alpha-synucleinopathy may be defined herein as an alpha-synucleinopathy having an association with the level and/or activity of GBA enzyme. In one embodiment the alpha-synucleinopathy presents with reduced GBA levels and/or activity, which is associated with an increase in alpha-synuclein. In one embodiment the treatment with arimoclomol reduces alpha-synuclein aggregation. In one embodiment the treatment with arimoclomol increases GBA activity and/or levels.

In one embodiment there is provided an active pharmaceutical ingredient selected from N-[2-hydroxy-3-(1-piperidinyl)-propoxy]-pyridine-1-oxide-3-carboximidoyl chloride, its stereoisomers and the acid addition salts thereof, for use in a method of treating a GBA-associated alpha-synucleinopathy selected from the group consisting of GBA-associated Parkinson's disease (PD), GBA-associated dementia with Lewi bodies (DLB) and GBA-associated multiple system atrophy (MSA).

In one embodiment there is provided an active pharmaceutical ingredient selected from N-[2-hydroxy-3-(1-piperidinyl)-propoxy]-pyridine-1-oxide-3-carboximidoyl chloride, its stereoisomers and the acid addition salts thereof, for use in a method of treating Parkinson's disease, in particular GBA-associated Parkinson's disease.

In one embodiment the GBA-associated Parkinson's disease is Parkinson's disease associated with reduced GBA enzyme levels and/or activity.

In one embodiment the GBA-associated Parkinson's disease is Parkinson's disease associated with one or more GBA gene mutations. In one embodiment the individual with GBA-associated Parkinson's disease remain clinically unaffected re Gaucher's disease.

In one embodiment the GBA-associated Parkinson's disease is Parkinson's disease associated with a heterozygous GBA gene mutation. In one embodiment the GBA-associated disorder is an individual having one or more heterozygous GBA gene mutations who remain clinically unaffected re Gaucher's disease.

In one embodiment the GBA-associated Parkinson's disease is Parkinson's disease associated with a homozygous GBA gene mutation. In one embodiment the GBA-associated disorder is an individual having one or more homozygous and/or compound heterozygous GBA gene mutations who remain clinically unaffected re Gaucher's disease.

In one embodiment the GBA-associated disorder is a genetically high-risk Parkinson's disease GBA genotype. In one embodiment the GBA-associated disorder is GBA-deficient Parkinson's disease (PD-GBA). In one embodiment the GBA-associated disorder is Parkinson's disease patients with heterozygous GBA alleles.). In one embodiment the GBA-associated disorder is Parkinson's disease patients with homozygous GBA alleles, clinically unaffected re Gaucher's disease.

In one embodiment the GBA-associated associated Parkinson's disease is Parkinson's disease associated with a GBA gene mutation selected from the group consisting of L444P, D409H, D409V, E235A, E340A, E326K, N370S, V394L, A456P, V460V, C342G, G325R, P415R, Y133*, F213I, N188S and IVS2+1G>A/N188S. Said one or more mutations in the GBA gene can be heterozygous, compound heterozygous or homozygous mutations. In one embodiment the individual presenting with the GBA gene mutation is clinically unaffected re Gaucher's disease.

In one embodiment the individual having GBA-associated associated Parkinson's disease has a GBA gene mutation selected from the group consisting of L444P, D409H, D409V, E235A, E340A, E326K, N370S, V394L, A456P, V460V, C342G, G325R, P415R, Y133*, F213I, N188S and IVS2+1G>A/N188S.

In one embodiment the GBA-associated associated Parkinson's disease is Parkinson's disease associated with a N370S GBA gene mutation.

In one embodiment the GBA-associated associated Parkinson's disease is Parkinson's disease associated with a heterozygous N370S GBA gene mutation (N370S/+).

In one embodiment the GBA-associated associated Parkinson's disease is Parkinson's disease associated with a homozygous N370S GBA gene mutation (N370S/N370S).

In one embodiment the GBA-associated associated Parkinson's disease is Parkinson's disease associated with a heterozygous L444P GBA gene mutation.

In one embodiment the GBA-associated associated Parkinson's disease is Parkinson's disease associated with a heterozygous A456P GBA gene mutation.

In one embodiment the GBA-associated associated Parkinson's disease is Parkinson's disease associated with a heterozygous V460V GBA gene mutation.

In one embodiment the GBA-associated associated Parkinson's disease is Parkinson's disease associated with a heterozygous E326K GBA gene mutation.

In one embodiment the GBA-associated disorder is Parkinson's disease associated with idiopathic reduced GBA activity and/or levels. In one embodiment the GBA-associated disorder is Parkinson's disease with idiopathic reduced GBA activity and/or levels, wherein no GBA gene mutations are identified.

Also provided herewith is an active pharmaceutical ingredient selected from N-[2-hydroxy-3-(1-piperidinyl)-propoxy]-pyridine-1-oxide-3-carboximidoyl chloride, its stereoisomers and the acid addition salts thereof, for use in a method of one or more of
- increasing GBA activity,
- increasing GBA levels (or amount),
- increasing the amount of active mutant GBA,
- increasing the amount of active wild type GBA,
- enhancing folding of ER-retained mutant GBA,
- increasing the amount of processed/maturated GBA,
- increasing the amount of matured (post-ER) GBA, and/or
- increasing the amount of matured GBA reaching the lysosomes.

In one embodiment arimoclomol is for use in a method of increasing GBA levels and/or activity in an individual having a GBA-associated disorder, such as a GBA-associated alpha-synucleinopathy, such as GBA-associated Parkinson's disease.

In one embodiment said GBA activity is increased to 50% or more of hypothetical wild-type activity levels, such as 50-60%, such as 60-70%, such as 70-80%, such as 80-90%, such as 90-100%, such as 100-110%, such as 110-120%, such as 120-130%, such as 130-140%, such as 140-150% of hypothetical wild-type activity levels.

In one embodiment said GBA activity is increased to hypothetical wild-type activity levels or more.

In one embodiment said GBA activity is increased at least 10%, such as at least 20%, for example at least 30%, such as at least 40%, for example at least 50%, such as at least 60%, for example at least 70%, such as at least 80%, for example at least 90%, such as at least 100%, for example at least 110%, such as at least 120%, for example at least 130%, such as at least 140%, for example at least 150%, such as at least 160%, for example at least 170%, such as at least 180%, for example at least 190%, such as at least 200%, for example at least 210%, such as at least 220%, for example at least 230%, such as at least 240%, for example at least 250%, such as at least 260%, for example at least 200%, such as at least 270%, for example at least 280%, such as at least 290%, for example at least 300%.

In one embodiment said GBA level (or amount) is increased to 50% or more of hypothetical wild-type levels, such as 50-60%, such as 60-70%, such as 70-80%, such as 80-90%, such as 90-100%, such as 100-110%, such as 110-120%, such as 120-130%, such as 130-140%, such as 140-150% of hypothetical wild-type levels.

In one embodiment said GBA level is increased to hypothetical wild-type levels or more.

In one embodiment said GBA level and/or activity is increased at least 1.5-fold, such as at least 2-fold, for example at least 2.5-fold, such as at least 3-fold.

In one embodiment said GBA level (or amount) is increased at least 10%, such as at least 20%, for example at least 30%, such as at least 40%, for example at least 50%, such as at least 60%, for example at least 70%, such as at least 80%, for example at least 90%, such as at least 100%, for example at least 110%, such as at least 120%, for example at least 130%, such as at least 140%, for example at least 150%, such as at least 160%, for example at least 170%, such as at least 180%, for example at least 190%, such as at least 200%, for example at least 210%, such as at least 220%, for example at least 230%, such as at least 240%, for example at least 250%, such as at least 260%, for example at least 200%, such as at least 270%, for example at least 280%, such as at least 290%, for example at least 300%.

Also provided herewith is an active pharmaceutical ingredient selected from N-[2-hydroxy-3-(1-piperidinyl)-propoxy]-pyridine-1-oxide-3-carboximidoyl chloride, its stereoisomers and the acid addition salts thereof, for use in a method of reducing alpha-synuclein aggregation.

Preventive Use

In another aspect there is provided an active pharmaceutical ingredient selected from N-[2-hydroxy-3-(1-piperidinyl)-propoxy]-pyridine-1-oxide-3-carboximidoyl chloride, its stereoisomers and the acid addition salts thereof, for use in a method of reducing risk in an individual of developing a glucocerebrosidase (GBA)-associated disorder other than Gaucher's disease, wherein said individual has reduced GBA enzyme level and/or activity.

In one embodiment said individual has GBA levels and/or activity lower than hypothetical wild-type levels.

In one embodiment said individual has GBA levels (or amount) lower than hypothetical wild-type levels.

In one embodiment said individual has GBA activity lower than hypothetical wild-type activity levels.

In one embodiment said individual has GBA levels and/or activity higher than clinically affected levels and/or activity in a patient with Gaucher's disease.

In one embodiment said individual has GBA levels and/or activity lower than hypothetical wild-type levels and/or activity, yet higher than clinically affected levels and/or activity in a patient with Gaucher's disease.

In one embodiment said individual has reduced GBA activity to the same degree as a GBA gene mutation carrier (heterozygous GBA mutation), such as a clinically unaffected carrier, such as an obligate carrier.

In one embodiment said individual has reduced GBA levels to the same degree as a GBA gene mutation carrier (heterozygous GBA mutation), such as a clinically unaffected carrier, such as an obligate carrier.

In one embodiment said individual with reduced GBA levels and/or activity has one or more heterozygous GBA gene mutations.

In one embodiment said individual with reduced GBA levels and/or activity has one or more homozygous or compound heterozygous GBA gene mutations.

In one embodiment said individual has reduced GBA activity and/or level to a certain extent of hypothetical wild type levels.

In one embodiment said individual has GBA activity and/or levels of about 5 to 95% or 10 to 90% of hypothetical wild type levels, such as 5 to 10%, such as 10 to 20%, such as 20 to 30%, such as 30 to 40%, such as 40 to 50%, such as 50 to 60%, such as 60 to 70%, such as 70 to 80%, such as 80 to 90%, such as 90 to 95% of hypothetical wild type activity and/or levels.

In one embodiment said individual has GBA activity and/or levels of about 25 to 75% of hypothetical wild type levels. In one embodiment said individual has GBA activity and/or levels of about 50% of hypothetical wild type levels.

In one embodiment said individual has GBA activity and/or levels of about 10 of hypothetical wild type levels and/or activity, such as 20%, such as 30%, such as 40%, such as 50%, such as 60%, such as 70%, such as 80%, such as 90% of hypothetical wild type levels and/or activity.

In one embodiment said GBA-associated disorder is a GBA-associated alpha-synucleinopathy, such as a GBA-associated alpha-synucleinopathy selected from the group consisting of GBA-associated Parkinson's disorder (PD), GBA-associated dementia with Lewi bodies (DLB) and GBA-associated multiple system atrophy (MSA).

In one embodiment there is provided an active pharmaceutical ingredient selected from N-[2-hydroxy-3-(1-piperidinyl)-propoxy]-pyridine-1-oxide-3-carboximidoyl chloride, its stereoisomers and the acid addition salts thereof, for use in a method of reducing risk in an individual of developing Parkinson's disease, in particular GBA-associated Parkinson's disease, wherein said individual has reduced GBA enzyme levels and/or activity.

In one embodiment said individual has one or more heterozygous GBA gene mutations. In one embodiment said individual has one or more heterozygous GBA gene mutations selected from the group consisting of L444P, D409H, D409V, E235A, E340A, E326K, N370S, N370S/1-BP ins 84G, V394L, A456P, V460V, C342G, G325R, P415R, Y133*, F213I, N188S and IVS2+1G>A/N188S. In one embodiment said individual has a heterozygous L444P GBA gene mutation. In one embodiment said individual has a heterozygous E326K GBA gene mutation. In one embodiment said individual has a heterozygous N370S GBA gene mutation.

In one embodiment said individual has one or more homozygous GBA gene mutations. In one embodiment said individual has one or more homozygous GBA gene mutations selected from the group consisting of L444P, D409H, D409V, E235A, E340A, E326K, N370S, N370S/1-BP ins 84G, V394L, A456P, V460V, C342G, G325R, P415R, Y133*, F213I, N188S and IVS2+1G>A/N188S. In one embodiment said individual has a homozygous N370S GBA gene mutation.

In one embodiment there is provided an active pharmaceutical ingredient selected from N-[2-hydroxy-3-(1-piperidinyl)-propoxy]-pyridine-1-oxide-3-carboximidoyl chloride, its stereoisomers and the acid addition salts thereof, for use in a method of reducing risk in an individual of developing GBA-associated Parkinson's disease, wherein said individual is a patient with Gaucher's disease, such as Gaucher's disease type I, type II or type III.

GBA Activity

Glucocerebrosidase activity can be assessed by methods known in the art. For example, the glucocerebrosidase activity may be measured from the cerebral spinal fluid of mammals. In some embodiments, the mammal is wild-type for the GBA gene. The term "wild-type" refers to a gene or protein with no detectable mutations known to affect the level and/or enzymatic activity of the protein.

When the gene is found to be wild-type, but a reduction in glucocerebrosidase activity is observed, the reduction in activity may be due to suppression of activity of the protein or repression of transcription or translation of the gene/protein. These mechanisms are well known in the art. For example, the production of the protein may be repressed by aberrant cellular mechanism. Alternatively, the protein may be modified in the cell which causes reduced or loss of enzymatic activity.

Arimoclomol

Reference to arimoclomol herein encompasses an active pharmaceutical ingredient (API) selected from N-[2-hydroxy-3-(1-piperidinyl)-propoxy]-pyridine-1-oxide-3-carboximidoyl chloride (arimoclomol), its stereoisomers and the acid addition salts thereof. Arimoclomol is further described in e.g. WO 00/50403.

Arimoclomol refers to the base compound N-[2-hydroxy-3-(1-piperidinyl)-propoxy]-pyridine-1-oxide-3-carboximidoyl chloride, its optically active (+) or (−) enantiomer, a mixture of the enantiomers of any ratio, and the racemic compound, furthermore, the acid addition salts formed from any of the above compounds with mineral or organic acids constitute objects of the present invention. All possible geometrical isomer forms of N-[2-hydroxy-3-(1-piperidinyl)-propoxy]-pyridine-1-oxide-3-carboximidoyl chloride belong to the scope of the invention. The term "the stereoisomers of N-[2-hydroxy-3-(1-piperidinyl)-propoxy]-pyridine-1-oxide-3-carboximidoyl chloride" refers to all possible optical and geometrical isomers of the compound.

If desired, the N-[2-hydroxy-3-(1-piperidinyl)-propoxy]-pyridine-1-oxide-3-carboximidoyl chloride or one of its optically active enantiomers can be transformed into an acid addition salt with a mineral or organic acid, by known methods.

In one embodiment the active pharmaceutical ingredient is the racemate of N-[2-hydroxy-3-(1-piperidinyl)-propoxy]-pyridine-1-oxide-3-carboximidoyl chloride.

In one embodiment the active pharmaceutical ingredient is an optically active stereoisomer of N-[2-hydroxy-3-(1-piperidinyl)-propoxy]-pyridine-1-oxide-3-carboximidoyl chloride.

In one embodiment the active pharmaceutical ingredient is an enantiomer of N-[2-hydroxy-3-(1-piperidinyl)-propoxy]-pyridine-1-oxide-3-carboximidoyl chloride.

In one embodiment the active pharmaceutical ingredient is selected from the group consisting of (+)-R—N-[2-hydroxy-3-(1-piperidinyl)-propoxy]-pyridine-1-oxide-3-carboximidoyl chloride and (−)-(S)—N-[2-hydroxy-3-(1-piperidinyl)-propoxy]-pyridine-1-oxide-3-carboximidoyl chloride.

In one embodiment the active pharmaceutical ingredient is an acid addition salt of N-[2-hydroxy-3-(1-piperidinyl)-propoxy]-pyridine-1-oxide-3-carboximidoyl chloride.

In one embodiment the active pharmaceutical ingredient is selected from the group consisting of N-[2-hydroxy-3-(1-piperidinyl)-propoxy]-pyridine-1-oxide-3-carboximidoyl chloride citrate (also known as BRX-345), and N-[2-hydroxy-3-(1-piperidinyl)-propoxy]-pyridine-1-oxide-3-carboximidoyl chloride maleate (also known as BRX-220).

In one embodiment the active pharmaceutical ingredient is selected from the group consisting of (+)-R—N-[2-hydroxy-3-(1-piperidinyl)-propoxy]-pyridine-1-oxide-3-carboximidoyl chloride citrate; (−)-S—N-[2-hydroxy-3-(1-piperidinyl)-propoxy]-pyridine-1-oxide-3-carboximidoyl chloride citrate; (+)-R—N-[2-hydroxy-3-(1-piperidinyl)-propoxy]-pyridine-1-oxide-3-carboximidoyl chloride maleate; and (−)-S—N-[2-hydroxy-3-(1-piperidinyl)-propoxy]-pyridine-1-oxide-3-carboximidoyl chloride maleate.

Composition

Whilst it is possible for the active pharmaceutical ingredient to be administered as the raw chemical, it is in some embodiments preferred to present them in the form of a pharmaceutical formulation. Accordingly, also provided herewith is a composition, such as a pharmaceutical composition, i.e. a pharmaceutically safe composition, comprising an active pharmaceutical ingredient as defined herein. The composition in one embodiment comprises a pharmaceutically and/or physiologically acceptable carriers or excipients.

Pharmaceutical compositions containing a bioactive agent of the present invention may be prepared by conventional techniques, e.g. as described in Remington: The Science and Practice of Pharmacy, 20$^{th}$ Edition, Gennaro, Ed., Mack Publishing Co., Easton, Pa., 2000.

It is thus an aspect to provide a composition, such as a pharmaceutical composition, comprising an active pharmaceutical ingredient selected from N-[2-hydroxy-3-(1-piperidinyl)-propoxy]-pyridine-1-oxide-3-carboximidoyl chloride, its stereoisomers and the acid addition salts thereof (arimoclomol), for use in the treatment of a glucocerebrosidase (GBA)-associated disorder other than Gaucher's disease (GD) as defined herein.

Administration and Dosage

An active pharmaceutical ingredient or composition comprising the same as defined herein is in one embodiment administered to individuals in need thereof in pharmaceutically effective doses or a therapeutically effective amount.

A therapeutically effective amount of an active pharmaceutical ingredient is in one embodiment an amount sufficient to cure, prevent, reduce the risk of, alleviate or partially arrest the clinical manifestations of a given disease or disorder and its complications. The amount that is effective for a particular therapeutic purpose will depend on the severity and the sort of the disorder as well as on the weight and general state of the subject. An amount adequate to accomplish this is defined as a "therapeutically effective amount".

In one embodiment, the composition is administered in doses of 1 µg/day to 100 mg/day; such as 1 µg/day to 10 µg/day, such as 10 µg/day to 100 µg/day, such as 100 µg/day to 250 µg/day, such as 250 µg/day to 500 µg/day, such as 500 µg/day to 750 µg/day, such as 750 µg/day to 1 mg/day, such as 1 mg/day to 2 mg/day, such as 2 mg/day to 5 mg/day, or such as 5 mg/day to 10 mg/day, such as 10 mg/day to 20 mg/day, such as 20 mg/day to 30 mg/day, such as 30 mg/day to 40 mg/day, such as 40 mg/day to 50 mg/day, such as 50 mg/day to 75 mg/day, such as 75 mg/day to 100 mg/day, such as 100 mg/day to 150 mg/day, such as 150 mg/day to 200 mg/day, or such as 200 mg/day to 250 mg/day, such as 250 mg/day to 300 mg/day, such as 300 mg/day to 400 mg/day, such as 400 mg/day to 500 mg/day, such as 500 mg/day to 600 mg/day, such as 600 mg/day to 700 mg/day, such as 700 mg/day to 800 mg/day, such as 800 mg/day to 900 mg/day, such as 900 mg/day to 1000 mg/day.

In one embodiment, the active pharmaceutical ingredient or composition is administered at a dose of 1 µg/kg body weight to 100 mg/kg body weight; such as 1 to 10 µg/kg body weight, such as 10 to 100 µg/day, such as 100 to 250 µg/kg body weight, such as 250 to 500 µg/kg body weight, such as 500 to 750 µg/kg body weight, such as 750 µg/kg body weight to 1 mg/kg body weight, such as 1 mg/kg body weight to 2 mg/kg body weight, such as 2 to 5 mg/kg body weight, such as 5 to 10 mg/kg body weight, such as 10 to 20 mg/kg body weight, such as 20 to 30 mg/kg body weight, such as 30 to 40 mg/kg body weight, such as 40 to 50 mg/kg body weight, such as 50 to 75 mg/kg body weight, or such as 75 to 100 mg/kg body weight.

In one embodiment, a dose is administered one or several times per day, such as from 1 to 6 times per day, such as from 1 to 5 times per day, such as from 1 to 4 times per day, such as from 1 to 3 times per day, such as from 1 to 2 times per day, such as from 2 to 4 times per day, such as from 2 to 3 times per day. In one embodiment, a dose is administered less than once a day, such as once every second day or once a week.

Routes of Administration

It will be appreciated that the preferred route of administration will depend on the general condition and age of the subject to be treated, the nature of the condition to be treated, the location of the tissue to be treated in the body and the active ingredient chosen.

Systemic Treatment

In one embodiment, the route of administration allows for introducing the bioactive agent into the blood stream to ultimately target the sites of desired action.

In one embodiment the routes of administration is any suitable route, such as an enteral route (including the oral, rectal, nasal, pulmonary, buccal, sublingual, transdermal, intracisternal and intraperitoneal administration), and/or a parenteral route (including subcutaneous, intramuscular, intrathecal, intravenous and intradermal administration).

Appropriate dosage forms for such administration may be prepared by conventional techniques.

Parenteral Administration

Parenteral administration is any administration route not being the oral/enteral route whereby the bioactive agent avoids first-pass degradation in the liver. Accordingly, parenteral administration includes any injections and infusions, for example bolus injection or continuous infusion, such as intravenous administration, intramuscular administration or subcutaneous administration. Furthermore, parenteral administration includes inhalations and topical administration.

Accordingly, the active pharmaceutical ingredient or composition is in one embodiment administered topically to cross any mucosal membrane of an animal, e.g. in the nose, vagina, eye, mouth, genital tract, lungs, gastrointestinal tract, or rectum, for example the mucosa of the nose, or mouth, and accordingly, parenteral administration may also include buccal, sublingual, nasal, rectal, vaginal and intraperitoneal administration as well as pulmonal and bronchial administration by inhalation or installation. In some embodiments, the bioactive agent is administered topically to cross the skin.

In one embodiment, the intravenous, subcutaneous and intramuscular forms of parenteral administration are employed.

Local Treatment

In one embodiment, the active pharmaceutical ingredient t or composition is used as a local treatment, i.e. is introduced directly to the site(s) of action. Accordingly, the active pharmaceutical ingredient may be applied to the skin or mucosa directly, or may be injected into the site of action, for example into the diseased tissue or to an end artery leading directly to the diseased tissue.

Combination Treatment

It is also an aspect to provide an active pharmaceutical ingredient selected from N-[2-hydroxy-3-(1-piperidinyl)-propoxy]-pyridine-1-oxide-3-carboximidoyl chloride, its stereoisomers and the acid addition salts thereof (arimoclomol), for use in a method of treating a glucocerebrosidase (GBA)-associated disorder other than Gaucher's disease (GD), in combination with other treatment modalities.

Thus, in one embodiment, the active pharmaceutical ingredient is administered to an individual in need thereof in combination with at least one other treatment modality, such as conventional or known treatment modalities for (GBA)-associated disorders including GBA-associated alpha-synucleinopathies such as GBA-associated Parkinson's disease (PD), GBA-associated dementia with Lewi bodies (DLB) and GBA-associated multiple system atrophy (MSA).

Administering more than one treatment modality in combination may occur either simultaneously, or sequentially. Simultaneous administration may be two compounds comprised in the same composition or comprised in separate compositions, or may be one composition and one other treatment modality performed essentially at the same time. Sequential administration means that the more than one treatment modalities are administered at different time points, such as administering one treatment modality first, and administering the second treatment modality subsequently. The time frame for administering more than one treatment modality sequentially may be determined by a skilled person in the art for achieving the optimal effect, and may in one embodiment be between 30 minutes to 72 hours.

The treatment modalities in the form of chemical compounds may be administered together or separately, each at its most effective dosage. Administering more than one compound may have a synergistic effect, thus effectively reducing the required dosage of each drug.

It is also an aspect to provide a composition comprising, separately or together, i) an active pharmaceutical ingredient selected from N-[2-hydroxy-3-(1-piperidinyl)-propoxy]-pyridine-1-oxide-3-carboximidoyl chloride, its stereoisomers and the acid addition salts thereof (arimoclomol), and ii) other treatment modalities, for use in the treatment of (GBA)-associated disorders including GBA-associated alpha-synucleinopathies such as GBA-associated Parkinson's disease (PD), GBA-associated dementia with Lewi bodies (DLB) and GBA-associated multiple system atrophy (MSA).

In one embodiment other treatment modalities, or conventional or known treatment modalities, are referred to as further active ingredients.

In one embodiment the active pharmaceutical ingredient selected from N-[2-hydroxy-3-(1-piperidinyl)-propoxy]- pyridine-1-oxide-3-carboximidoyl chloride, its stereoisomers and the acid addition salts thereof (arimoclomol), is administered in combination with, and/or formulated as a combination product, with one or more further active ingredients.

In one embodiment the further active ingredient is selected from one or more active ingredients known and/or employed in the treatment of (GBA)-associated disorders including GBA-associated alpha-synucleinopathies such as GBA-associated Parkinson's disease (PD), GBA-associated dementia with Lewi bodies (DLB) and GBA-associated multiple system atrophy (MSA).

In one embodiment the further active ingredient is a compound used for the treatment of Parkinson's disease. In one embodiment said compound used for the treatment of Parkinson's disease is selected from the group consisting of dopamine, L-DOPA, levodopa, dopamine receptor agonists, carboxylase inhibitors such as carbidopa or benserazide, NMDA antagonists such as for example amatidine (Symmetrel), catechol-O-methyl transferase (COMT) inhibitors such as for example tolcapone and entacapone, MAO-B inhibitors such as for example selegiline and rasagiline, Carbidopa-levodopa, Anticholinergics and Amantadine.

In one embodiment the further active ingredient is a compound used for the treatment of Gaucher's disease. In one embodiment the further active ingredient is selected from the group consisting of enzyme replacement therapies, allosteric chaperones, pharmacological chaperones and substrate reduction therapies. In one embodiment said further active ingredient is selected from the group consisting of miglustat (Zavesca), imiglucerase (Cerezyme), eliglustat (Cerdelga), VPRIV, taliglucerase alfa (Elelyso) and velaglurase alpha.

EXAMPLES

Example 1: Dose-Dependent Response in Gaucher Type II Heterozygotes (Parkinsons Disease Genotype)—BiP and GBA Induction Materials and Methods
Cell Culture Primary human fibroblast cell lines were cultured under standard cell culture conditions (37° C. and 5% $CO_2$) in DMEM supplemented with non-essential amino acids (NEAA), 1% Pen-Strep and 12% FCS. They were passaged 1-2 times/week with a split ratio of 1:2 or 1:3. Cells were used for experiments around passage 16-26 where no signs of replicative senescence were observed (visual inspection).

| Cell line | GBA mutation | Age at Sampling | GD type |
|---|---|---|---|
| GM00877 | L444P/L444P, A456P, V460V | 1 Y | II |
| GM00878 | L444P, A456P, V460V | — | carrier |

Western Blotting

Cells were collected in PBS and centrifuged at 3500 rpm for 5 min at 4° C. Cell pellets were lysed in 1× Extraction buffer (Enzo Life Science) containing protease inhibitors, sonicated and cleared by centrifugation at 13000 rpm for 10 min at 4° C. Protein concentration measured by the BCA assay. Samples containing approx. 10-20 µg protein were diluted in glycoprotein denaturing buffer (New England Biolabs) and denatured by incubation for 10 min at 100° C. Samples were incubated with or without EndoH (New England Biolabs) for 1 h at 37° C., Laemmli sample buffer was added and the samples were subjected to SDS-PAGE using the TGX gel system (Bio-Rad). After transfer to a nitrocellulose membrane (Trans-Blot Turbo, Bio-Rad), the membranes were stained briefly with Ponceau S, and subsequently blocked in 5% skim-milk in PBS+0.1% tween (PBS-T). Incubation with primary antibodies (1:500 to 1:2000 dilution) was performed on parafilm-coated glass plates overnight at 4° C. After washing in PBS-T the membranes were incubated 1 h with secondary antibody diluted 1:10,000 in 5% skim milk in PBS-T. The blots were developed using SuperSignal™ West Dura Extended Duration Substrate (Life technologies) and visualized using a G-box system (Syngene).

Results

Arimoclomol-induced dose-dependent increase in ER Hsp70 (BiP) in primary cells Arimoclomol is reported to increase the expression levels of heat-shock proteins, e.g. heat-shock protein 70 (HSP70) (Kieran et al., Nature Medicine, 2004).

To assess the effect of arimoclomol on the ER Hsp70 (BiP) expression level in primary cells, human fibroblasts from individual with a heterozygous GBA allele containing the L444P,A456P,V460V mutations in cis (carrier, clinically unaffected re. Gaucher's disease) were treated with 0, 10, 50 or 200 µM arimoclomol for 14 days. Cells were then harvested for western blot analysis. A lysate from untreated normal human fibroblasts was used for control.

Our results demonstrate that arimoclomol dose-dependently increases BiP expression levels in a human fibroblasts cell line heterozygous for the complex GBA allele L444P, A456P,V460V. This suggests that arimoclomol via BiP-upregulation can lead to an enhanced folding of ER-retained mutant GBA.

Arimoclomol-Induced Dose-Dependent Increase in GBA Enzyme Amount in Primary Cells The effect of arimoclomol on GBA protein levels was also evaluated in the human fibroblasts cell line heterozygous for the complex GBA allele L444P,A456P,V460V. In line with an upregulation of the ER chaperone BiP, a dose-dependent increase in the total level of GBA is seen in arimoclomol-treated cells.

Example 2: Dose-Dependent Response on GBA Activity in Gaucher Type II Homozygotes and Heterozygotes (GTII and High-Risk Parkinsons Disease Genotype Materials and Methods
Cell Culture Primary human fibroblast cell lines were cultured under standard cell culture conditions (37° C. and 5% $CO_2$) in DMEM supplemented with non-essential amino acids (NEAA), 1% Pen-Strep and 12% FCS. They were passaged 1-2 times/week with a split ratio of 1:2 or 1:3. Cells were used for experiments around passage 16-26 where no signs of replicative senescence were observed (visual inspection).

GBA Activity Assay

GBA activity was measured using the "intact cell" GBA assay using the 4-Methylumbelliferyl beta-D-glucopyranoside (4-MUG) substrate (Mu et al, Cell, 2008). Briefly, fibroblasts were seeded in 12 well plates and treated in biological triplicate with indicated concentrations of arimoclomol for 4 weeks. Medium was replenished with fresh compound every 2-3 days and the cells were split twice during the experiment. After 4 weeks of treatment, cells were transferred to 96 well plates and GBA activity was measured using 4-MUG as substrate at pH 4.0. The released 4-MU fluorophore was quantified as Fluorescence Units (FLU) and normalized to cell density using crystal violet staining of a parallel plate. The normalized data is reported as Arbitrary Units (mean±SD).

Results

Figure 3:
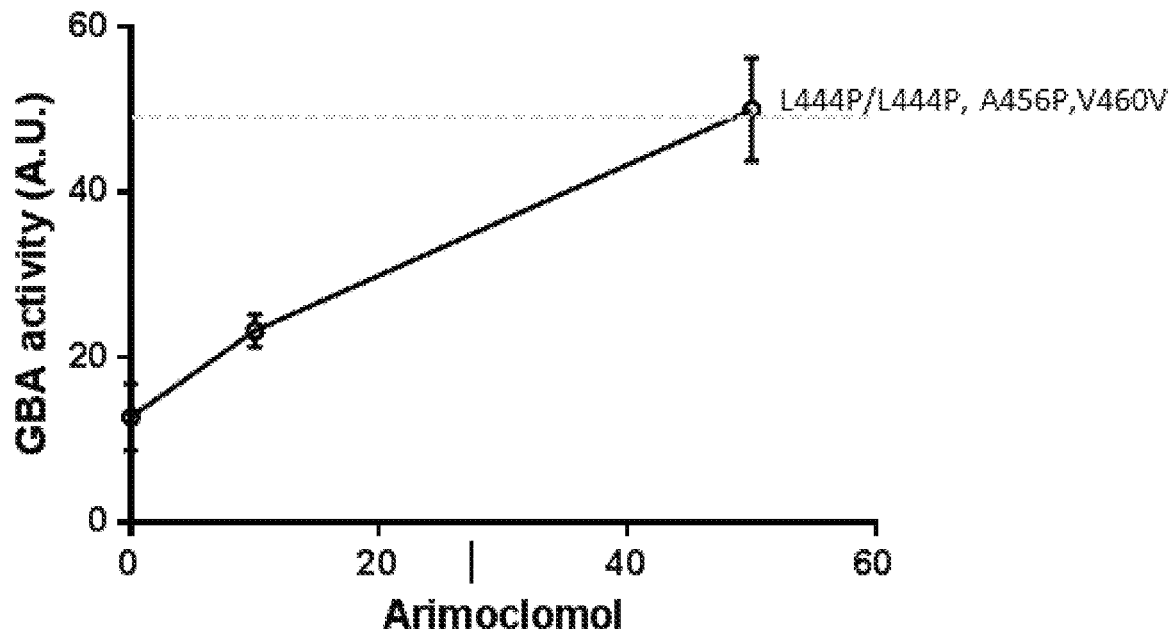
FIG. 3: Arimoclomol-induced dose-dependent increase in GBA activity in L444P/L444P,A456P,V460V Gaucher TII patient. Level increased to clinically unaffected activity level (dashed line). See Example 2.
Figure 4:
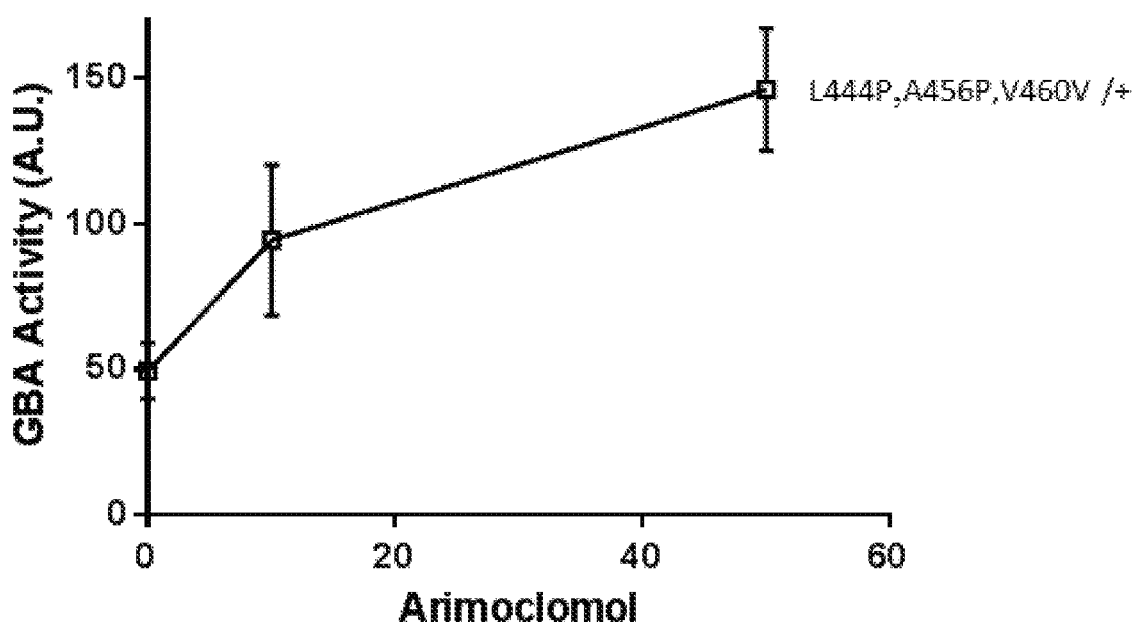
FIG. 4: Arimoclomol-induced dose-dependent increase in GBA activity in L444P,A456P,V460V Heterozygote (carrier; clinically unaffected parent of Gaucher disease patient, genetically high-risk Parkinson's disease genotype). Level increased by more than 2-fold. See Example 2.
Figure 5:
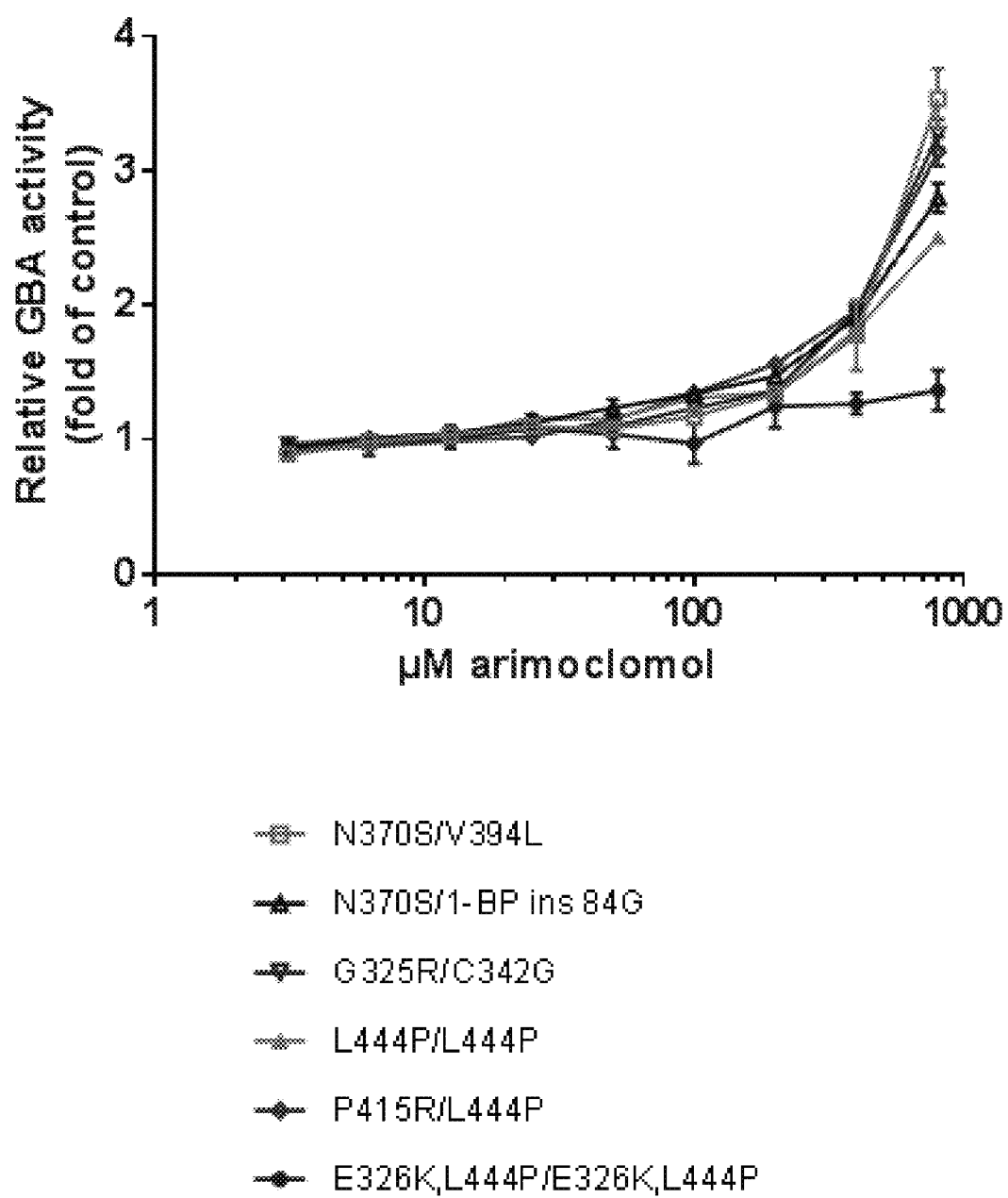
FIG. 5: Arimoclomol-induced dose-dependent increase in GBA activity in primary cells from Gaucher disease patients of type I (N370S/V394L and N370S/1-BP ins 84G), type II (E326K, L444P/E326K, L444P and G325R/C342G and P415R/L444P) or type III (L444P/L444P). See Example 3.
Figure 6:
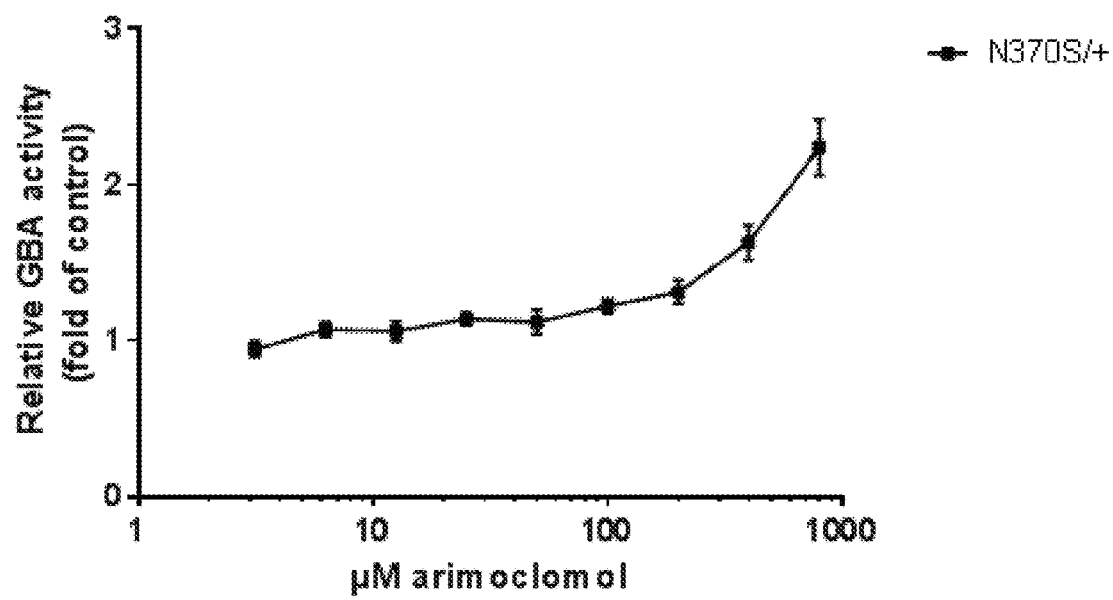
FIG. 6: Arimoclomol-induced dose-dependent increase in GBA activity in primary cells from Parkinson Disease patient with a heterozygous GBA allele containing the N370S mutation (N370S/+). See Example 4.
Figure 7:
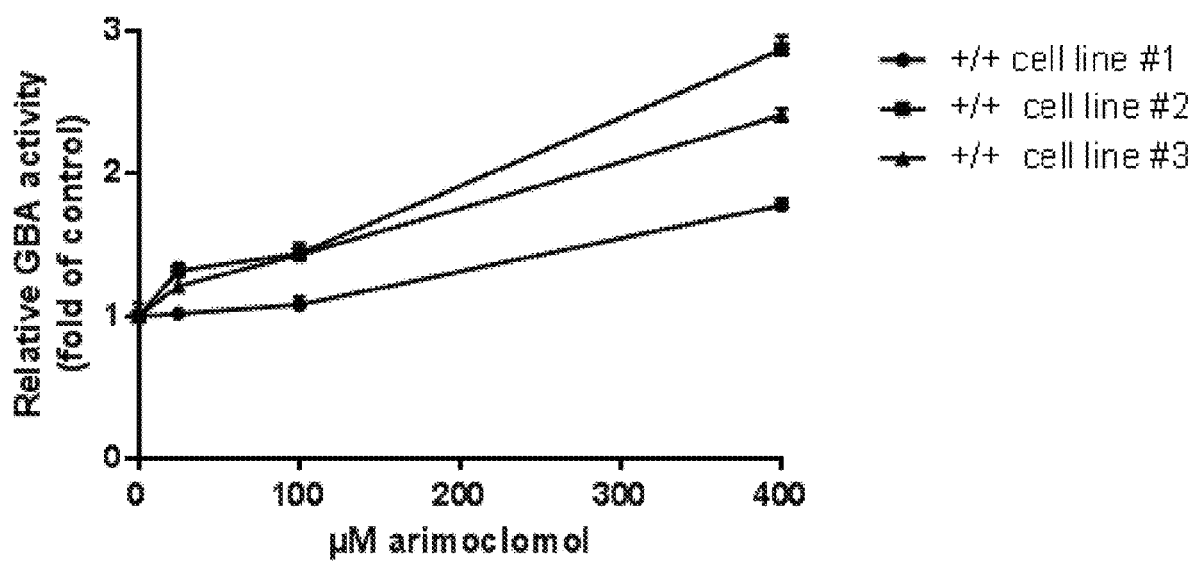
FIG. 7: Arimoclomol-induced dose-dependent increase in GBA activity in human fibroblasts from non-symptomatic healthy individuals with no GBA mutation (+/+). See Example 5.
Figure 8:
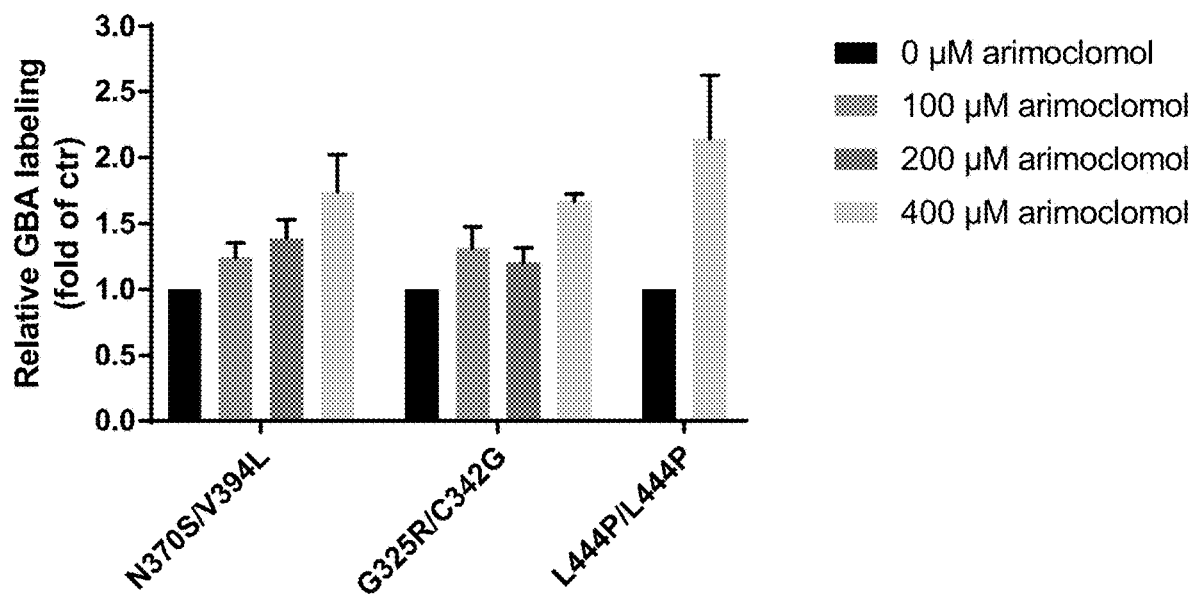
FIG. 8: Arimoclomol-induced increase in labeling of active GBA by ME569 in primary cells from Gaucher disease patients of type I (N370S/V394L), type II (G325R/C342G) and type III (L444P/L444P). See Example 6.
Figure 9:
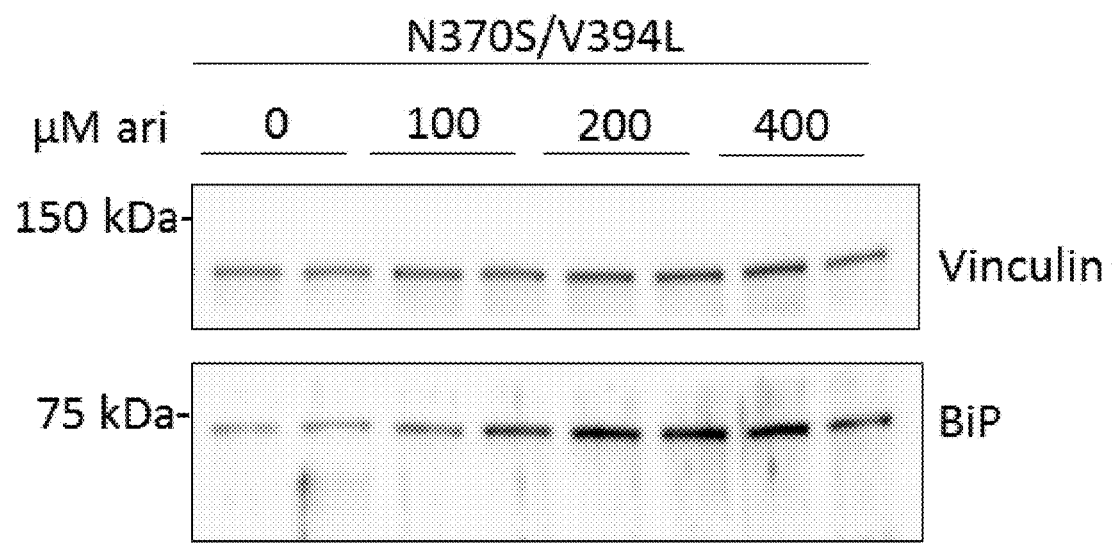
FIG. 9: Arimoclomol-induced dose-dependent increase in ER Hsp70 (BiP) in primary cells from Gaucher disease patient of type I (N370S/V394L). Vinculin was used as loading control. See Example 7.
Figure 10:
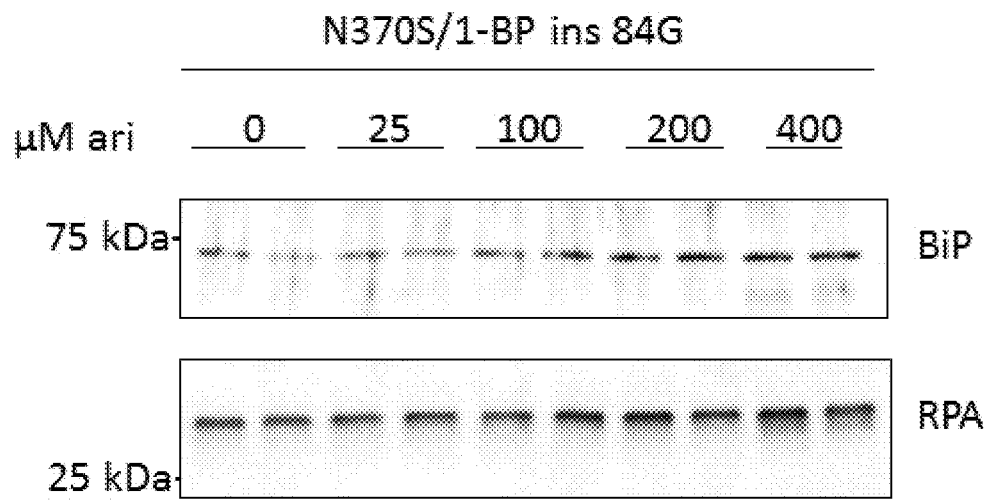
FIG. 10: Arimoclomol-induced dose-dependent increase in ER Hsp70 (BiP) in in primary cells from Gaucher disease patient of type I (N370S/1-BP ins 84G). RPA was used as loading control. See Example 7.
Figure 11:
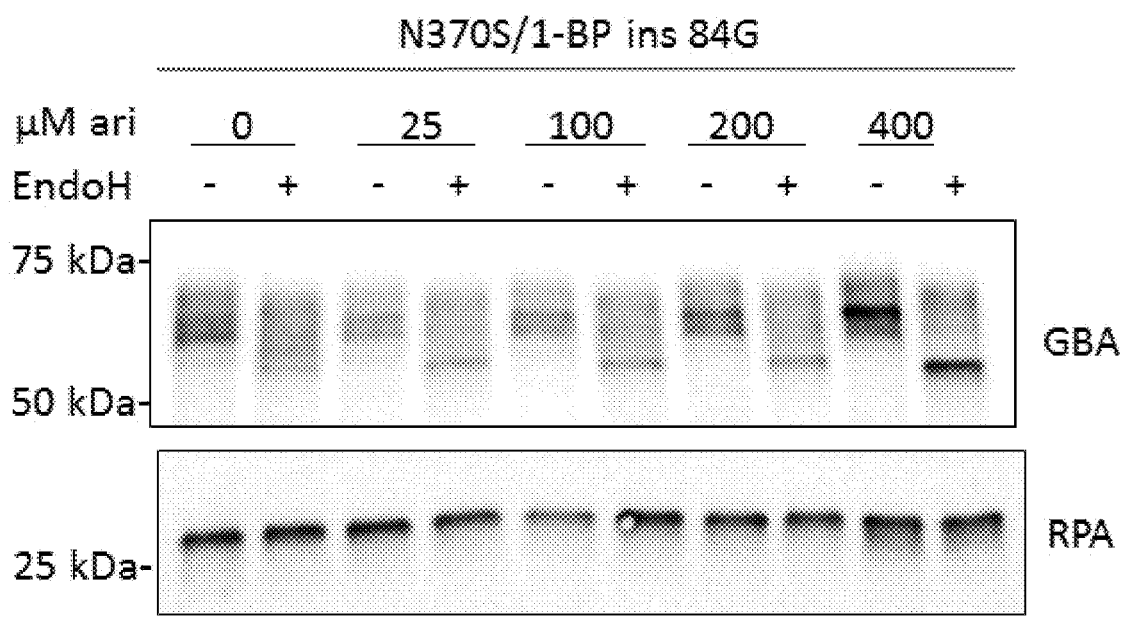
FIG. 11: Arimoclomol-induced dose-dependent increase in GBA protein level in primary cells from Gaucher disease patient of type I (N370S/1-BP ins 84G). RPA was used as loading control. See Example 7.
Figure 12:
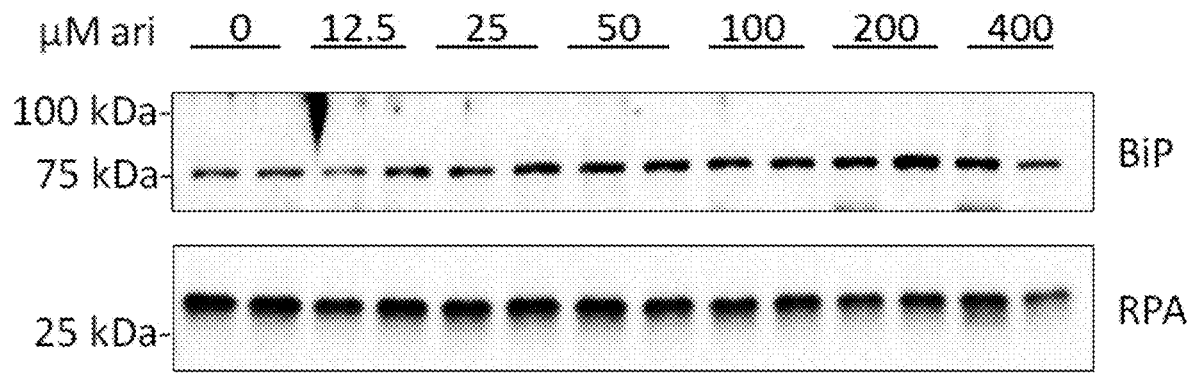
FIG. 12: Arimoclomol-induced dose-dependent increase in ER Hsp70 (BiP) in primary cells from Gaucher disease patient of type II (L444P/P415R). RPA was used as loading control. See Example 8.
Figure 13:
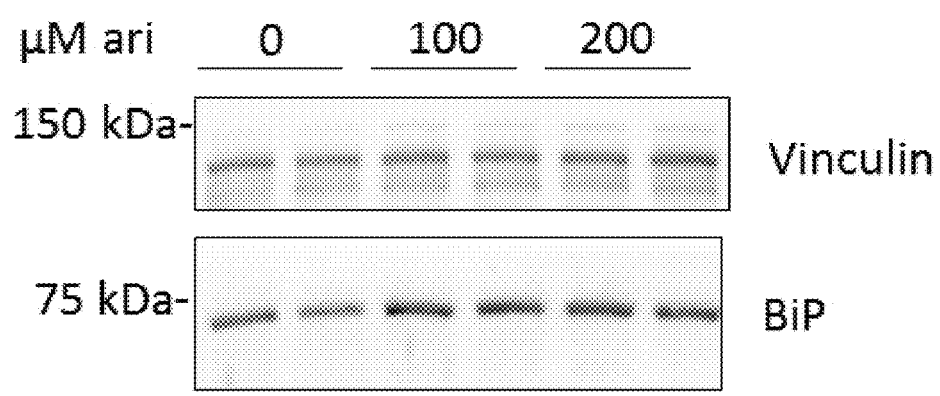
FIG. 13: Arimoclomol-induced increase in ER Hsp70 (BiP) in primary cells from Gaucher disease patient of type II (G325R/C342G). Vinculin was used as loading control. See Example 8.
Figure 14:
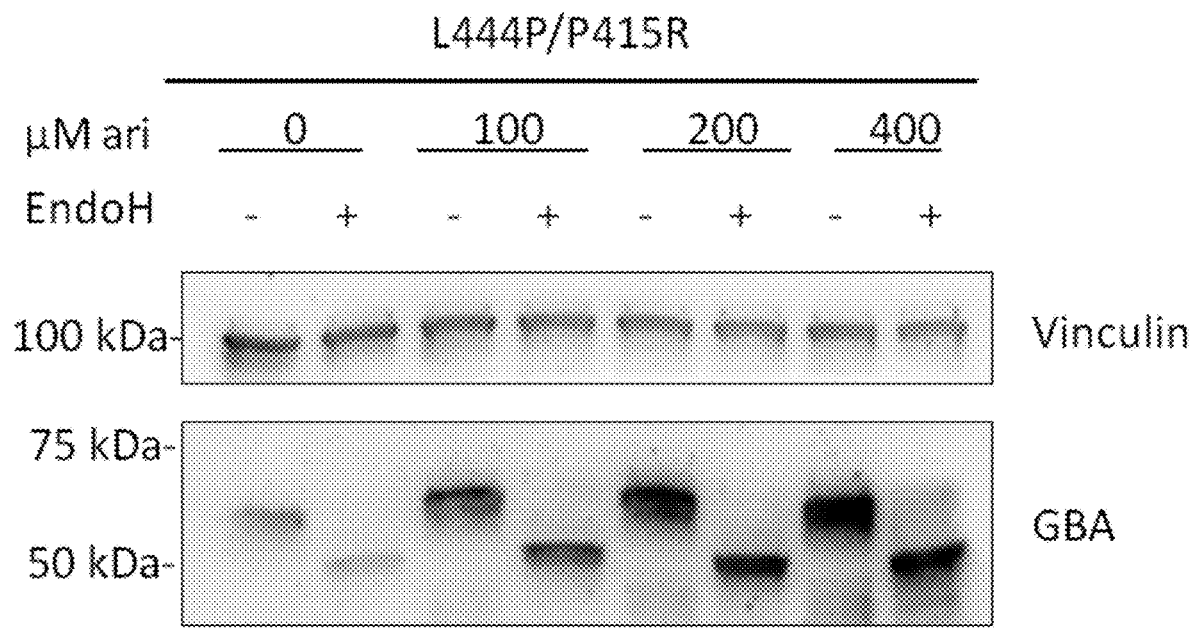
FIG. 14: Arimoclomol-induced dose-dependent increase in GBA protein level in primary cells from Gaucher disease patient of type II (L444P/P415R). Vinculin was used as loading control. See Example 8.
Figure 15:
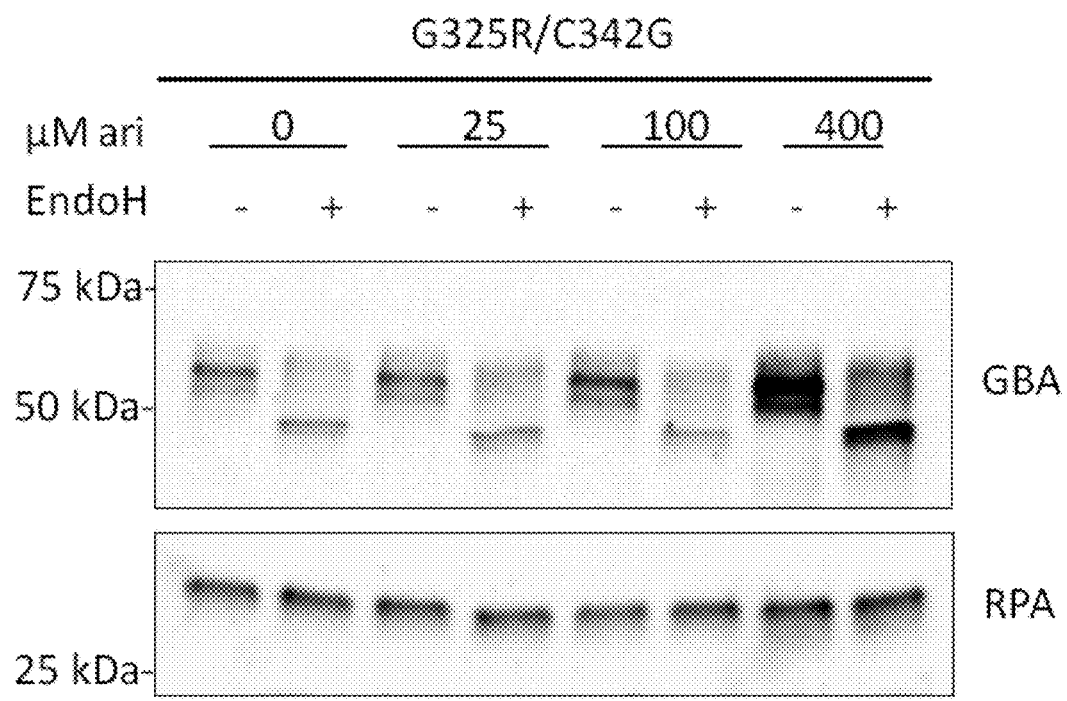
FIG. 15: Arimoclomol-induced dose-dependent increase in GBA protein level in primary cells from Gaucher disease patient of type II (G325R/C342G). RPA was used as loading control. See Example 8.
Figure 16:
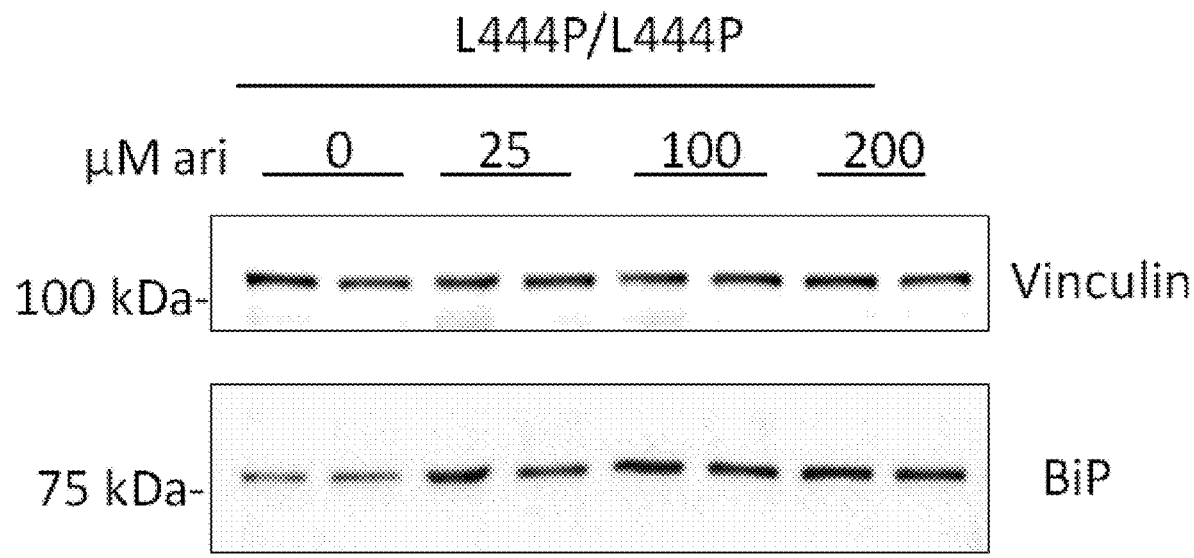
FIG. 16: Arimoclomol-induced dose-dependent increase in ER Hsp70 (BiP) in primary cells from Gaucher disease patient of type III (L444P/L444P). Vinculin was used as loading control. See Example 9.
Figure 17:
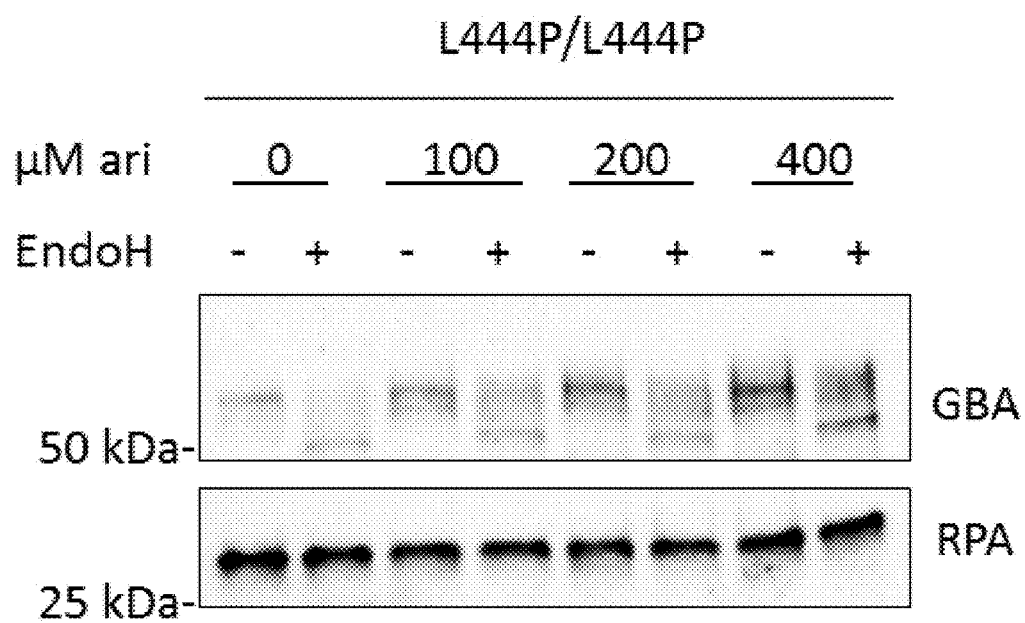
FIG. 17: Arimoclomol-induced dose-dependent increase in GBA protein level in primary cells from Gaucher disease patient of type III (L444P/L444P). RPA was used as loading control. See Example 9.
Figure 18:
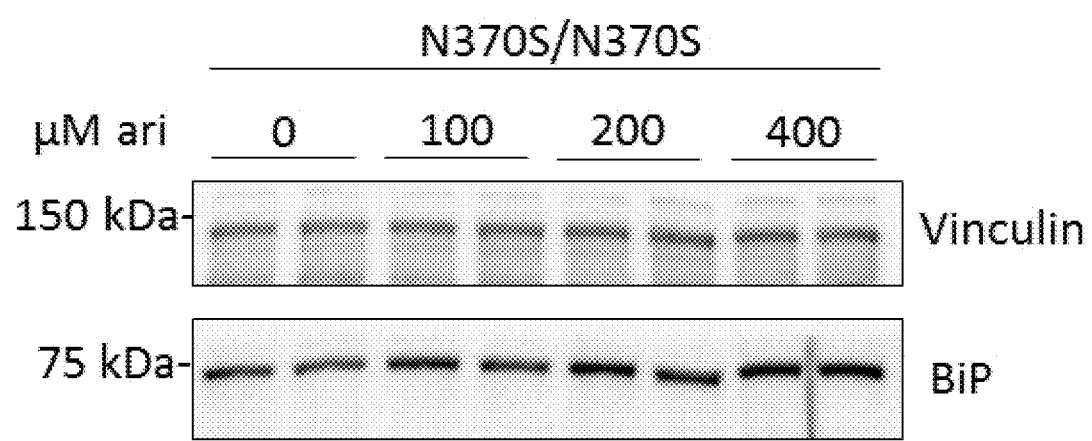
FIG. 18: Arimoclomol-induced dose-dependent increase in ER Hsp70 (BiP) in primary cells from a PD-GBA (N370S/N370S) individual. Vinculin was used as loading control. See Example 10.
Figure 19A:
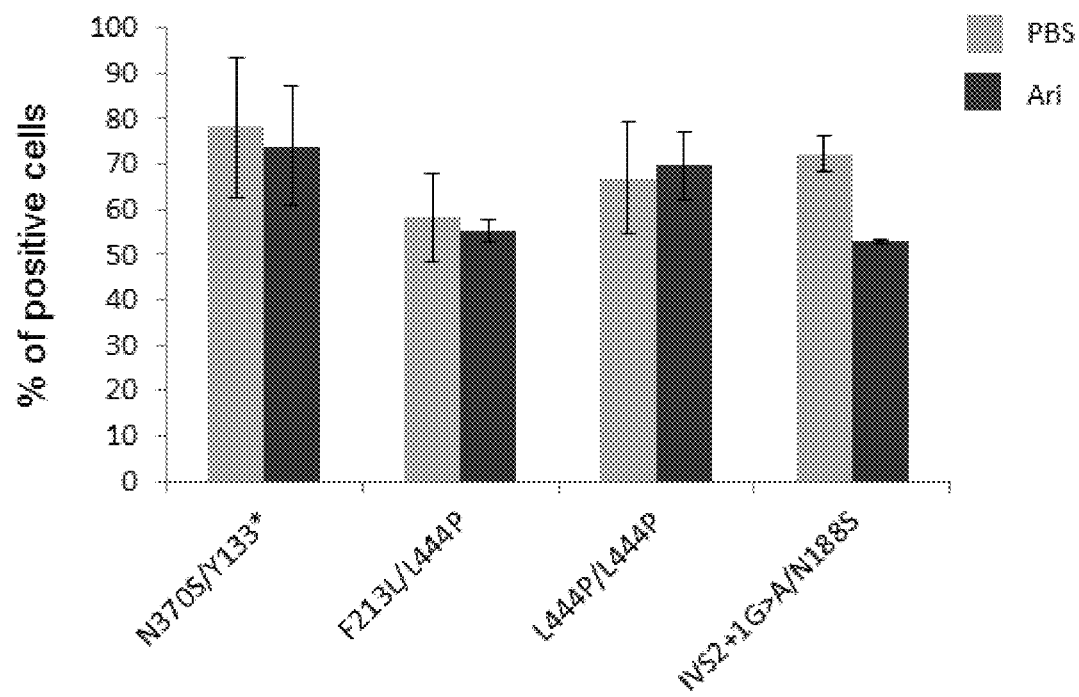
FIGS. 19A and 19B: Arimoclomol does not affect neuronal differentiation of MASCs from GD individuals with the indicated GBA mutations. Cells were either treated with mock (PBS) or 400 μM arimoclomol (Ari) for 9 days. The expression of the neuronal markers Tubulin beta 3 (see FIG. 19 A) and NeuN (see FIG. 19 B) was evaluated by immunostaining. See Example 11.
Figure 19B:
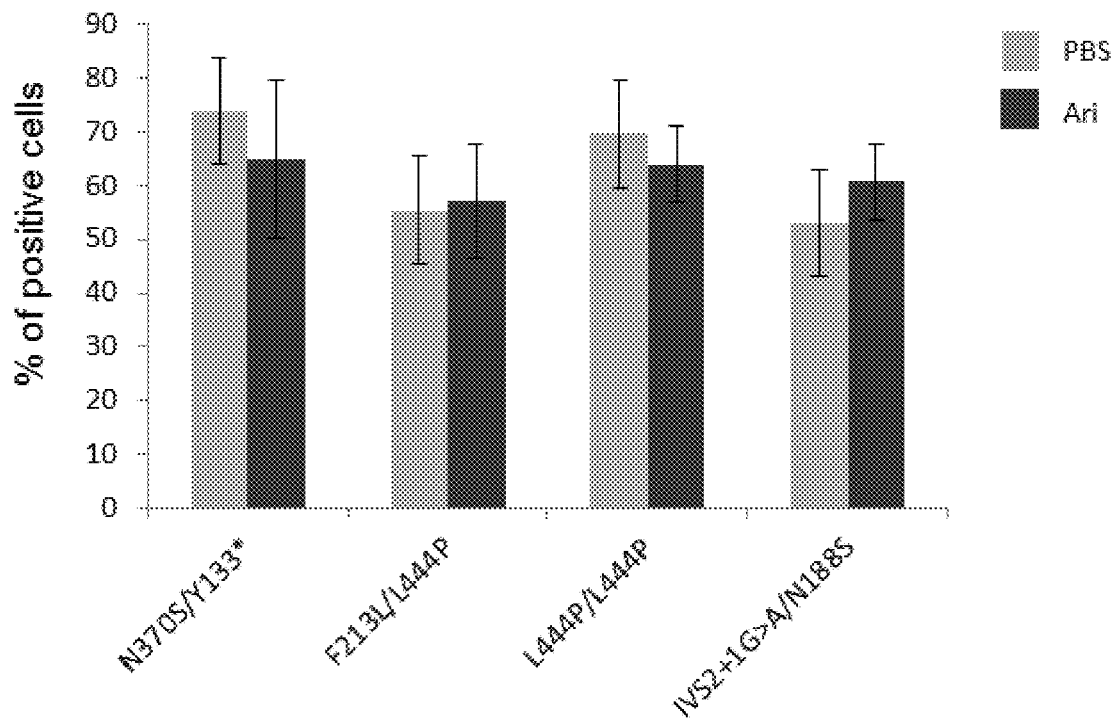
Figure 20:
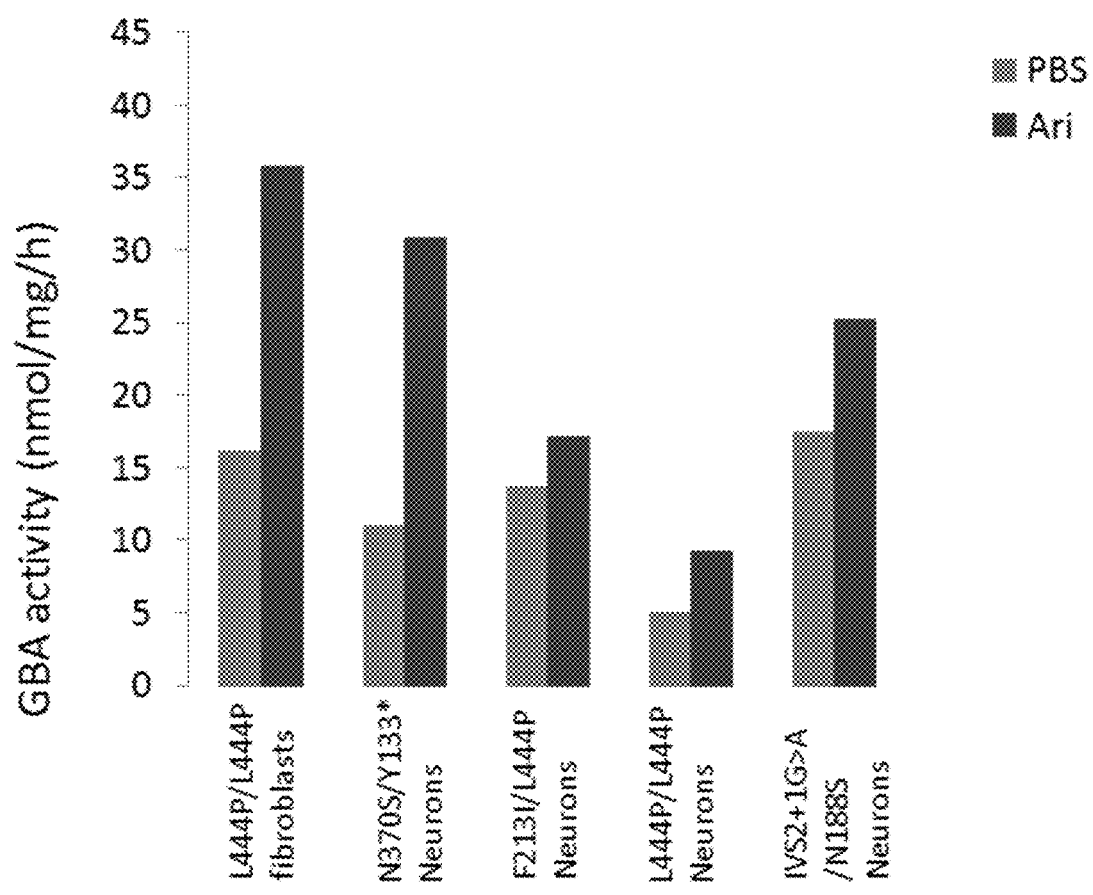
FIG. 20: Arimoclomol-induced increase in GBA activity in primary neronal-like cells from GD individuals with the indicated GBA mutations. Skin-derived fibroblasts from individual with GDTIII (L444P/L444P) were included as control. Cells were either treated with mock (PBS) or 400 μM arimoclomol (Ari). See Example 11.

The effect of arimoclomol on GBA activity in primary cells with mutations of GBA was evaluated in fibroblasts from a Type II Gaucher patient with the genotype L444P/L444P,A456P,V460V. We observed that arimoclomol treatment increased GBA activity in a dose-dependent manner. Notably, the increase in GBA activity induced by 50 µM arimoclomol corresponds to the activity level of cells heterozygous for the L444P,A456P,V460V allele (marked by grey line in FIG. 3) from a non-symptomatic individual.

Importantly, arimoclomol also increases the GBA activity in primary fibroblasts that are heterozygous for the L444P, A456P,V460V allele. This result demonstrates that GBA activity can be increased even in cells from mutant GBA heterozygotes (carriers).

Example 3: Dose-Dependent Response on GBA Activity in Gaucher Type I, Type II and Type II Homozygotes Materials and Methods
Cell Culture Primary human fibroblast cell lines were cultured under standard cell culture conditions (37° C. and 5% $CO_2$) in DMEM supplemented with non-essential amino acids (NEAA), 1% Pen-Strep and 12% FCS. They were passaged 1-2 times/week with a split ratio of 1:2 or 1:3. Cells were used for experiments around passage 16-26 where no signs of replicative senescence were observed (visual inspection).

| Cell line | GBA mutation | Age at Sampling | Disease |
|---|---|---|---|
| GM08760 | L444P, E326K/L444P, E326K | 1 Y | GD TII |
| GM10915 | L444P/L444P | 7 Y | GD TIII |
| GM01607 | N370S/V394L | 30 Y | GD TI |
| GM00372 | N370S/1-BP ins 84G | 29 Y | GD TI |
| GM02627 | G325R/C342G | 3 Y | GD TII |
| GM01260 | L444P/P415R | 11 M | GD TII |

GBA Activity Assay

GBA activity was measured using the "intact cell" GBA assay using the 4-Methylumbelliferyl beta-D-glucopyranoside (4-MUG) substrate (Mu et al, Cell, 2008). Briefly, fibroblasts were seeded in 96 well plates and treated in biological triplicate with indicated concentrations of arimoclomol for 5 days. Medium was replenished with fresh compound every 2-3 days. GBA activity was measured using 4-MUG as substrate at pH 4.0. The released 4-MU fluorophore was quantified as Fluorescence Units (FLU) and normalized to cell density using crystal violet staining of a parallel plate. The normalized data is reported as fold change relative to mock-treated control cells (mean±SD).

Results

The effect of arimoclomol on GBA activity in primary cells with additional mutations of GBA was evaluated by treating cells of the indicated genotype with arimoclomol. Our data show that arimoclomol dose-dependently increases GBA activity in two GD type I cell lines: N370S/V394L and N370S/1-BP ins 84G. Importantly, since the 1-BP ins 84G is considered to be a null-allele, these results demonstrate that arimoclomol increases the activity of the N370S mutation.

A dose-dependent effect of arimoclomol is also seen for GBA activity in primary cells from GD type II/III patients which are either homozygotes for L444P (L444P/L444P) or compound heterozygotes for the GBA mutations G325R/C342G or P415R/L444P. A less pronounced increase of GBA activity is found in arimoclomol-treated type II GD cells homozygous for the E326K, L444P allele.

Example 4: Dose-Dependent Response on GBA Activity in Primary Cells from a Parkinson Disease Patient with a Heterozygous GBA Allele Containing the N370S Mutation Materials and Methods
Cell Culture The primary human fibroblast cell line was cultured under standard cell culture conditions (37° C. and 5% $CO_2$) in DMEM supplemented with non-essential amino acids (NEAA), 1% Pen-Strep and 12% FCS. The cells were passaged 1 time/week with a split ratio of 1:2. Cells were used for experiments around passage 16-26 where no signs of replicative senescence were observed (visual inspection).

| Cell line | GBA mutation | Age at Sampling | Disease |
|---|---|---|---|
| ND34263 | N370S | 65 Y | PD |

GBA Activity Assay

GBA activity was measured using the "intact cell" GBA assay using the 4-Methylumbelliferyl beta-D-glucopyranoside (4-MUG) substrate (Mu et al, Cell, 2008). Briefly, fibroblasts were seeded in 96 well plates and treated in biological triplicate with indicated concentrations of arimoclomol for 5 days. Medium was replenished with fresh compound every 2-3 days. GBA activity was measured using 4-MUG as substrate at pH 4.0. The released 4-MU fluorophore was quantified as Fluorescence Units (FLU) and normalized to cell density using crystal violet staining of a parallel plate. The normalized data is reported as fold change relative to mock-treated control cells (mean±SD).

Results

To investigate the effect of arimoclomol on the N370S mutation in Parkinson disease, primary cells from a PD patient with N370S mutation was treated with arimoclomol. Our data show that arimoclomol dose-dependently increases N370S GBA activity in cells from a PD patient.

Example 5: Dose-Dependent Response on GBA Activity in Primary Cells from Healthy Individuals without GBA Mutations (+/+)

Materials and Methods
Cell Culture

Primary human fibroblast cell lines were cultured under standard cell culture conditions (37° C. and 5% $CO_2$) in DMEM supplemented with non-essential amino acids (NEAA), 1% Pen-Strep and 12% FCS. They were passaged 1-2 times/week with a split ratio of 1:2 or 1:3. Cells were used for experiments around passage 16-26 where no signs of replicative senescence were observed (visual inspection).

| Cell line | GBA mutation | Age at Sampling | Disease |
|---|---|---|---|
| GM00498 | — | 3 Y | — |
| GM05659 | — | 1 Y | — |
| GM08401 | — | 75 Y | — |

GBA Activity Assay

GBA activity was measured using the "intact cell" GBA assay using the 4-Methylumbelliferyl beta-D-glucopyranoside (4-MUG) substrate (Mu et al, Cell, 2008). Briefly, fibroblasts were seeded in 96 well plates and treated in biological triplicate with indicated concentrations of arimoclomol for 5 days. Medium was replenished with fresh compound every 2-3 days. GBA activity was measured using 4-MUG as substrate at pH 4.0. The released 4-MU fluorophore was quantified as Fluorescence Units (FLU) and normalized to cell density using crystal violet staining of a parallel plate. The normalized data is reported as fold change relative to mock-treated control cells (mean±SD).

Results

To investigate the effect of arimoclomol on WT GBA protein, primary cells from healthy individuals without GBA mutations (+/+) were treated with arimoclomol. We observed that arimoclomol treatment increased WT GBA activity in a dose-dependent manner in all three cell lines albeit to different magnitude.

Example 6: Arimoclomol-Induced Increase in Activity-Based Probe Labeling of Active GBA in Gaucher Disease TI/TII/TIII Materials and Methods Cell Culture Primary human fibroblast cell lines were cultured under standard cell culture conditions (37° C. and 5% CO2) in DMEM supplemented with non-essential amino acids (NEAA), 1% Pen-Strep and 12% FCS. They were passaged 1-2 times/week with a split ratio of 1:2 or 1:3. Cells were used for experiments around passage 16-26 where no signs of replicative senescence were observed (visual inspection).

| Cell line | GBA mutation | Age at Sampling | Disease |
|---|---|---|---|
| GM01607 | N370S/V394L | 30 Y | GD TI |
| GM02627 | G325R/C342G | 3 Y | GD TII |
| GM10915 | L444P/L444P | 7 Y | GD TIII |

GBA Labeling with ME569

Active GBA can be selectively labeled with the fluorescent activity-based probe (ABP) ME569 (Witte et al, 2010). Briefly, fibroblasts were seeded in dishes and treated in biological duplicates with the indicated concentrations of arimoclomol for 5 days. Medium was replenished with fresh compound every 2-3 days. Cells were collected in PBS, proteins were extracted and the concentrations were determined using the BCA assay. Equal amount of total protein was incubated with ME569 for 30 minutes at 37° C. Loading buffer was added, samples were incubated for 5 min at 98° C. and then subjected to SDS-PAGE using the TGX gel system (Bio-Rad). After gel electrophoresis, fluorescence was detected using red LEDs/705M filter (G-box, Syngene). The amount of labeled GBA was quantified using the software GeneTools v.4.03.01.0 from Syngene. The normalized data is reported as fold change relative to mock-treated control cells (mean±SEM, n=3-4).

Results

The effect of arimoclomol on the amount of GBA labeled with fluorescent ABP was evaluated in primary cells from GD patients of the indicated genotype. Our data show that arimoclomol dose-dependently increases GBA labeling in the GD TI cell line (N370S/V394L) and the GD TII cell line (G325R/C342G). Only the high dose of arimoclomol was evaluated in the GD TII cell line (homozygotes for L444P) and also in this cell line, arimoclomol increases the amount of GBA that can be labeled with fluorescent ABP. Taken together, these data show that arimoclomol increases the amount of active mutant GBA in primary cells from all three types of Gaucher Disease (TI type 1, TII type II and TIII type III).

Example 7: Dose-Dependent Response in Gaucher Type I—BiP and GBA Induction

Materials and Methods

Cell Culture

Primary human fibroblast cell lines were cultured under standard cell culture conditions (37° C. and 5% $CO_2$) in DMEM supplemented with non-essential amino acids (NEAA), 1% Pen-Strep and 12% FCS. They were passaged 1-2 times/week with a split ratio of 1:2 or 1:3. Cells were used for experiments around passage 16-26 where no signs of replicative senescence were observed (visual inspection).

| Cell line | GBA mutation | Age at Sampling | GD type |
|---|---|---|---|
| GM00372 | N370S/1-BP ins 84G | 29 Y | I |
| GM01607 | N370S/V394L | 30 Y | I |

Western Blotting

Cells were collected in PBS and centrifuged at 3500 rpm for 5 min at 4° C. Cell pellets were lysed in lysis buffer (Enzo Life Science) containing protease inhibitors, sonicated and cleared by centrifugation at 13000 rpm for 10 min at 4° C. Protein concentration was measured by the BCA assay. Samples containing approx. 10-20 µg protein were diluted in glycoprotein denaturing buffer (New England Biolabs) and denatured by incubation for 10 min at 100° C. Samples were incubated with or without EndoH (New England Biolabs) for 1 h at 37° C., Laemmli sample buffer was added and the samples were subjected to SDS-PAGE using the TGX gel system (Bio-Rad). After transfer to a nitrocellulose membrane (Trans-Blot Turbo, Bio-Rad), the membranes were stained briefly with Ponceau S, and subsequently blocked in 5% skim-milk in PBS+0.1% tween (PBS-T). Incubation with primary antibodies (1:500 to 1:2000 dilution) was performed on parafilm-coated glass plates overnight at 4° C. After washing in PBS-T the membranes were incubated 1 h with secondary antibody diluted 1:10,000 in 5% skim milk in PBS-T. The blots were developed using SuperSignal™ West Dura Extended Duration Substrate (Life technologies) and visualized using a G-box system (Syngene).

Results

Arimoclomol-Induced Dose-Dependent Increase in ER Hsp70 (BiP) in Type/GD Primary Cells Arimoclomol is reported to increase the expression levels of heat-shock proteins, e.g. heat-shock protein 70 (HSP70) (Kieran et al., Nature Medicine, 2004). To assess the effect of arimoclomol on the ER Hsp70 (BiP) expression level in primary cells, human fibroblasts from GD TI patients were treated with 0, 25, 100, 200 or 400 μM arimoclomol (N370S/V394L) or 0, 100, 200 or 400 μM arimoclomol (N370S/1-BP ins 84G) for 5 days.

Cells were then harvested for western blot analysis.

Our results demonstrate that arimoclomol dose-dependently increases BiP expression levels in human fibroblasts cell lines from type I Gaucher individuals. This suggests that arimoclomol via BiP-upregulation can lead to an enhanced folding of ER-retained mutant GBA.

Arimoclomol-Induced Dose-Dependent Increase in GBA Enzyme Amount in Type/GD Primary Cells The effect of arimoclomol on GBA protein levels was also evaluated in the human fibroblasts cell line from a type I Gaucher patient with the N370S/1-BP ins 84G genotype. In line with an upregulation of the ER chaperone BiP, a dose-dependent increase in the total level of GBA is seen in arimoclomol-treated cells from this individual. Moreover, an increase in the EndoH-resistant fraction shows that arimoclomol increases the amount of processed/maturated GBA in the cell.

Example 8: Dose-Dependent Response in Gaucher Type II—BiP and GBA Induction

Materials and Methods

Cell Culture

Primary human fibroblast cell lines were cultured under standard cell culture conditions (37° C. and 5% $CO_2$) in DMEM supplemented with non-essential amino acids (NEAA), 1% Pen-Strep and 12% FCS. They were passaged 1-2 times/week with a split ratio of 1:2 or 1:3. Cells were used for experiments around passage 16-26 where no signs of replicative senescence were observed (visual inspection).

| Cell line | GBA mutation | Age at Sampling | GD type |
|---|---|---|---|
| GM01260 | L444P/P415R | 11 M | II |
| GM02627 | G325R/C342G | 3 Y | II |

Western Blotting

Cells were collected in PBS and centrifuged at 3500 rpm for 5 min at 4° C. Cell pellets were lysed in lysis buffer (Enzo Life Science) containing protease inhibitors, sonicated and cleared by centrifugation at 13000 rpm for 10 min at 4° C. Protein concentration was measured by the BCA assay. Samples containing approx. 10-20 μg protein were diluted in glycoprotein denaturing buffer (New England Biolabs) and denatured by incubation for 10 min at 100° C. Samples were incubated with or without EndoH (New England Biolabs) for 1 h at 37° C., Laemmli sample buffer was added and the samples were subjected to SDS-PAGE using the TGX gel system (Bio-Rad). After transfer to a nitrocellulose membrane (Trans-Blot Turbo, Bio-Rad), the membranes were stained briefly with Ponceau S, and subsequently blocked in 5% skim-milk in PBS+0.1% tween (PBS-T). Incubation with primary antibodies (1:500 to 1:2000 dilution) was performed on parafilm-coated glass plates overnight at 4° C. After washing in PBS-T the membranes were incubated 1 h with secondary antibody diluted 1:10,000 in 5% skim milk in PBS-T. The blots were developed using SuperSignal™ West Dura Extended Duration Substrate (Life technologies) and visualized using a G-box system (Syngene).

Results

Arimoclomol-Induced Dose-Dependent Increase in ER Hsp70 (BiP) in Type II GD Primary Cells To assess the effect of arimoclomol on the ER Hsp70 (BiP) expression level in primary cells, human fibroblasts from type II Gaucher disease patients were treated with the indicated concentrations of arimoclomol for 5 days. Cells were then harvested for western blot analysis.

Our results demonstrate that arimoclomol dose-dependently increases BiP expression levels in human fibroblasts cell lines from GD TII individuals with L444P/P415R or G325R/C342G genotypes. This suggests that arimoclomol via BiP-upregulation can lead to an enhanced folding of ER-retained mutant GBA in GD TII cells.

Arimoclomol-Induced Dose-Dependent Increase in GBA Enzyme Amount in GD TII Primary Cells The effect of arimoclomol on GBA protein levels and maturation was also evaluated in GD TII primary cell lines. In line with an upregulation of the ER chaperone BiP, a dose-dependent increase in the total level of GBA is seen in arimoclomol-treated cells from these individuals. Moreover, an increase in the EndoH-resistant fraction shows that arimoclomol increases the amount of matured (post-ER) GBA in GD type II cells.

Example 9: Dose-Dependent Response in Gaucher Type III—BiP and GBA Induction Materials and Methods Cell Culture Primary human fibroblast cells were cultured under standard cell culture conditions (37° C. and 5% $CO_2$) in DMEM supplemented with non-essential amino acids (NEAA), 1% Pen-Strep and 12% FCS. They were passaged 1-2 times/week with a split ratio of 1:2 or 1:3. Cells were used for experiments around passage 16-26 where no signs of replicative senescence were observed (visual inspection).

| Cell line | GBA mutation | Age at Sampling | GD type |
|---|---|---|---|
| GM10915 | L444P/L444P | 7 Y | III |

Western Blotting

Cells were collected in PBS and centrifuged at 3500 rpm for 5 min at 4° C. Cell pellets were lysed in lysis buffer (Enzo Life Science) containing protease inhibitors, sonicated and cleared by centrifugation at 13000 rpm for 10 min at 4° C. Protein concentration was measured by the BCA assay. Samples containing approx. 10-20 μg protein were diluted in glycoprotein denaturing buffer (New England Biolabs) and denatured by incubation for 10 min at 100° C. Samples were incubated with or without EndoH (New England Biolabs) for 1 h at 37° C., Laemmli sample buffer was added and the samples were subjected to SDS-PAGE using the TGX gel system (Bio-Rad). After transfer to a nitrocellulose membrane (Trans-Blot Turbo, Bio-Rad), the membranes were stained briefly with Ponceau S, and subsequently blocked in 5% skim-milk in PBS+0.1% tween (PBS-T). Incubation with primary antibodies (1:500 to 1:2000 dilution) was performed on parafilm-coated glass plates overnight at 4° C. After washing in PBS-T the membranes were incubated 1 h with secondary antibody diluted 1:10,000 in 5% skim milk in PBS-T. The blots were developed using SuperSignal™ West Dura Extended Duration Substrate (Life technologies) and visualized using a G-box system (Syngene).

Results

Arimoclomol-Induced Dose-Dependent Increase in ER Hsp70 (BiP) in GD TIII Primary Cells To assess the effect of arimoclomol on the ER Hsp70 (BiP) expression level in primary cells, human fibroblasts from an individual with type III Gaucher disease (L444P/L444P) were treated with the indicated concentrations of arimoclomol for 5 days. Cells were then harvested for western blot analysis.

Our results demonstrate that arimoclomol dose-dependently increases BiP expression levels in this cell line homozygous for L444P. This suggests that arimoclomol via BiP-upregulation can lead to an enhanced folding of ER-retained mutant GBA.

Arimoclomol-Induced Dose-Dependent Increase in GBA Enzyme Amount in GD TIII Primary Cells The effect of arimoclomol on GBA protein levels and maturation was also evaluated in the L444P/L444P GD TIII primary cell line. In line with an upregulation of the ER chaperone BiP, a dose-dependent increase in the total level of GBA is seen in arimoclomol-treated cells. Moreover, an increase in the EndoH-resistant fraction of GBA shows that arimoclomol increases the amount of maturated GBA in the GD TIII cells.

Taken together, these results show that GBA activity is increased by arimoclomol likely due to more mature GBA reaching the lysosomes.

Example 10: Dose-Dependent Response in BiP Expression in GBA-Deficient Parkinson Disease Materials and Methods Cell Culture Primary human fibroblast cells were cultured under standard cell culture conditions (37° C. and 5% $CO_2$) in DMEM supplemented with non-essential amino acids (NEAA), 1% Pen-Strep and 12% FCS. They were passaged 1-2 times/week with a split ratio of 1:2 or 1:3. Cells were used for experiments around passage 16-26 where no signs of replicative senescence were observed (visual inspection).

| Cell line | GBA mutation | Age at Sampling | |
|---|---|---|---|
| ND34263 | N370S/N370S | 65 Y | PD-GBA |

Western Blotting

Cells were collected in PBS and centrifuged at 3500 rpm for 5 min at 4° C. Cell pellets were lysed in lysis buffer (Enzo Life Science) containing protease inhibitors, sonicated and cleared by centrifugation at 13000 rpm for 10 min at 4° C. Protein concentration was measured by the BCA assay and the samples were subjected to SDS-PAGE using the TGX gel system (Bio-Rad). After transfer to a nitrocellulose membrane (Trans-Blot Turbo, Bio-Rad), the membranes were stained briefly with Ponceau S, and subsequently blocked in 5% skim-milk in PBS+0.1% tween (PBS-T). Incubation with primary antibodies (1:500 to 1:2000 dilution) was performed on parafilm-coated glass plates overnight at 4° C. After washing in PBS-T the membranes were incubated 1 h with secondary antibody diluted 1:10,000 in 5% skim milk in PBS-T. The blots were developed using SuperSignal™ West Dura Extended Duration Substrate (Life technologies) and visualized using a G-box system (Syngene).

Results

Arimoclomol-Induced Dose-Dependent Increase in ER Hsp70 (BiP) in PD-GBA Primary Cells To assess the effect of arimoclomol on the ER Hsp70 (BiP) expression level in primary cells from an individual with GBA-deficient Parkinson Disease (PD-GBA), human fibroblasts from an individual with PD-GBA (N370S/N370S) were treated with the indicated concentrations of arimoclomol for 5 days. Cells were then harvested for western blot analysis.

Our results demonstrate that arimoclomol dose-dependently increases BiP expression levels in primary cells from an individual with PD-GBA (N370S/N370S). This suggests that arimoclomol via BiP-upregulation leads to an enhanced folding of ER-retained mutant GBA.

Example 11: Effect of Arimoclomol on GBA Activity in Primary Neuronal-Like Cells from GDTI and GDTIII Individuals Materials and Methods Cell Culture Human multipotent adult stem cells (MASCs) were isolated from GD individuals from skin biopsies. The genotype of the MASCs is shown below. Cells were induced to differentiate along a neuronal fate as described in Bergamin et al. Orphanet Journal of Rare Diseases 2013. The surface immunophenotype of stem cells was analyzed by FACS. Stem cell and neuronal markers expression were evaluated by immunofluorescence.

| MASC Cell line | GBA mutation | GD type |
|---|---|---|
| 1 | N370S/Y133* | I |
| 2 | F213I/L444P | III |
| 3 | L444P/L444P | III |
| 4 | IVS2 + 1G > A/N188S | III |

The asterisk denotes a frameshift and consequential de novo stop codon

MASCs were induced to differentiate along the neuronal lineage at Day 0. At Day 1, cells were treated with mock (PBS) or 400 µM arimoclomol. Treatment persisted throughout differentiation for a total 9 days. At Day 9, differentiation was evaluated by immunofluorescence of neuronal markers. GBA activity was measured using the fluorogenic substrate 4-MUG.

Results

Arimoclomol does not Affect Neuronal Differentiation of Skin-Derived Human Multipotent Adult Stem Cells from GD TI and GDTIII Individuals To assess the effect of arimoclomol on neuronal differentiation, MASCs from GD individuals were induced to differentiate while treated with mock or arimoclomol. Our results show that the expression of the neuronal markers Tubulin beta 3 and NeuN was not affected by arimoclomol.

Arimoclomol-Induced Increase in GBA Activity in Neurons from GD TI and GDTIII Individuals We find that arimoclomol increases mutant GBA activity in neurons from an individual with GD type I (N370S/Y133*) and in three individuals with GD type III (F213I/L444P, L444P/L444P or IVS2+1 G>A/N188S).

Taken together, our results demonstrate that arimoclomol increases mutant GBA activity in neurons from GD TI and GD TIII individuals without affecting neuronal differentiation.

REFERENCES

Kieran, D., Kalmar, B., Dick, J. R. T., Riddoch-Contreras, J., Burnstock, G., & Greensmith, L. (2004). Treatment with arimoclomol, a coinducer of heat shock proteins, delays disease progression in ALS mice. Nature Medicine, 10(4), 402-405

Mu, T., Ong, D. S. T., Wang, Y., Balch, W. E., Yates, J. R., Segatori, L., & Kelly, J. W. (2008). Chemical and biological approaches synergize to ameliorate protein-folding diseases. Cell, 134(5), 769-81

Bergamin, N., Dardis, A., Beltrami, A., Cesselli, D., Rigo, S., Zampieri, S., . . . Beltrami, C. A. (2013). A human neuronal model of Niemann Pick C disease developed from stem cells isolated from patient's skin. Orphanet Journal of Rare Diseases, 8(1), 34.

Witte, M. D., Kallemeijn, W. W., Aten, J., Li, K.-Y., Strijland, A., Donker-Koopman, W. E., Aerts, J. M. F. G. (2010). Ultrasensitive in situ visualization of active glucocerebrosidase molecules. Nature Chemical Biology, 6(12), 907-13.

The invention claimed is:

1. A method of increasing glucocerebrosidase (GBA) level and/or activity in a cell by at least 10%, wherein the cell has one or more GBA gene mutation selected from L444P, D409H, D409V, E235A, E340A, E326K, N370S, N370S/1-BP ins 84G, V394L, A456P, V460V, C342G, G325R, P415R, Y133*, F213I, N188S, and IVS2+1G>A/N188S, comprising:
    contacting the cell with an active pharmaceutical ingredient selected from: N-[2-hydroxy-3-(1-piperidinyl)-propoxy]-pyridine-1-oxide-3-carboximidoyl chloride, a stereoisomer thereof, and an acid addition salt thereof.

2. The method of claim 1, wherein the cell has reduced levels and/or activity of GBA compared to a control.

3. The method of claim 1, wherein the GBA gene mutation is homozygous.

4. The method of claim 1, wherein the GBA gene mutation is heterozygous.

5. The method of claim 1, wherein the GBA gene mutation is compound heterozygous.

6. The method of claim 1, wherein the active pharmaceutical ingredient:

i) is a racemate of N-[2-hydroxy-3-(1-piperidinyl)-propoxy]-pyridine-1-oxide-3-carboximidoyl chloride; or ii) is an optically active stereoisomer of N-[2-hydroxy-3-(1-piperidinyl)-propoxy]-pyridine-1-oxide-3-carboximidoyl chloride; or iii) is an enantiomer of N-[2-hydroxy-3-(1-piperidinyl)-propoxy]-pyridine-1-oxide-3-carboximidoyl chloride; or iv) is selected from the group consisting of (+)-R—N-[2-hydroxy-3-(1-piperidinyl)-propoxy]-pyridine-1-oxide-3-carboximidoyl chloride, and (−)-(S)—N-[2-hydroxy-3-(1-piperidinyl)-propoxy]-pyridine-1-oxide-3-carboximidoyl chloride; or v) is an acid addition salt of N-[2-hydroxy-3-(1-piperidinyl)-propoxy]-pyridine-1-oxide-3-carboximidoyl chloride; or vi) is selected from the group consisting of N-[2-hydroxy-3-(1-piperidinyl)-propoxy]-pyridine-1-oxide-3-carboximidoyl chloride citrate, and N-[2-hydroxy-3-(1-piperidinyl)-propoxy]-pyridine-1-oxide-3-carboximidoyl chloride maleate; or vii) is selected from the group consisting of (+)-R—N-[2-hydroxy-3-(1-piperidinyl)-propoxy]-pyridine-1-oxide-3-carboximidoyl chloride citrate; (−)-S—N-[2-hydroxy-3-(1-piperidinyl)-propoxy]-pyridine-1-oxide-3-carboximidoyl chloride citrate; (+)-R—N-[2-hydroxy-3-(1-piperidinyl)-propoxy]-pyridine-1-oxide-3-carboximidoyl chloride maleate; and (−)-S—N-[2-hydroxy-3-(1-piperidinyl)-propoxy]-pyridine-1-oxide-3-carboximidoyl chloride maleate.

7. The method of claim 1, wherein the cell is in vitro or in vivo.

8. The method of claim 1, wherein the GBA level and/or activity is increased at least 1.5-fold.

9. The method of claim 1, wherein the active pharmaceutical ingredient is (+)-R—N-[2-hydroxy-3-(1-piperidinyl)-propoxy]-pyridine-1-oxide-3-carboximidoyl chloride citrate.

* * * * *